(12) United States Patent
Honore et al.

(10) Patent No.: US 11,045,123 B2
(45) Date of Patent: Jun. 29, 2021

(54) WEARABLE DEVICE WITH MULTIMODAL DIAGNOSTICS

(71) Applicant: Graftworx, Inc., South San Francisco, CA (US)

(72) Inventors: Francis Honore, San Francisco, CA (US); James Reich, San Francisco, CA (US); Anthony F. Flannery, Jr., Bainbridge Island, WA (US); Samit Kumar Gupta, Menlo Park, CA (US); Ramkumar Abhishek, Menlo Park, CA (US)

(73) Assignee: GRAFTWORX, Inc., San Francisco, CA (US)

( * ) Notice: Subject to any disclaimer, the term of this patent is extended or adjusted under 35 U.S.C. 154(b) by 228 days.

(21) Appl. No.: 16/082,249

(22) PCT Filed: Mar. 28, 2018

(86) PCT No.: PCT/US2018/024925
§ 371 (c)(1),
(2) Date: Sep. 4, 2018

(87) PCT Pub. No.: WO2018/183558
PCT Pub. Date: Oct. 4, 2018

(65) Prior Publication Data
US 2020/0330011 A1 Oct. 22, 2020

Related U.S. Application Data

(60) Provisional application No. 62/626,559, filed on Feb. 5, 2018, provisional application No. 62/478,469, filed on Mar. 29, 2017.

(51) Int. Cl.
*A61B 5/1455* (2006.01)
*A61B 5/024* (2006.01)
(Continued)

(52) U.S. Cl.
CPC ........ *A61B 5/14552* (2013.01); *A61B 5/0261* (2013.01); *A61B 5/02427* (2013.01);
(Continued)

(58) Field of Classification Search
None
See application file for complete search history.

(56) References Cited

U.S. PATENT DOCUMENTS

2007/0255357 A1  11/2007 Rose et al.
2008/0050830 A1  2/2008 Floriano et al.
(Continued)

FOREIGN PATENT DOCUMENTS

EP         2848196 A1    3/2015
WO     WO-0021435 A1    4/2000
(Continued)

OTHER PUBLICATIONS

"International Application Serial No. PCT US2018 024925, International Search Report dated Jul. 26, 2018", 4 pgs.
(Continued)

*Primary Examiner* — Eric F Winakur
*Assistant Examiner* — Marjan Fardanesh
(74) *Attorney, Agent, or Firm* — Wilson Sonsini Goodrich & Rosati

(57) ABSTRACT

Systems and methods to non-invasively measure sub-cutaneous processes in a patient are disclosed. Examples of systems may optically detect biological fluid properties. The optical detection techniques described herein may be incorporated into a wearable monitoring system. Examples of wearable monitoring systems may simultaneously measure a plurality of sensory modalities. Systems of the present disclosure may be mounted on the skin of a patient.

13 Claims, 18 Drawing Sheets

(51) Int. Cl.
*A61B 5/026* (2006.01)
*A61B 5/145* (2006.01)
*A61B 5/00* (2006.01)
*A61M 1/36* (2006.01)

(52) U.S. Cl.
CPC ........ *A61B 5/1455* (2013.01); *A61B 5/14535* (2013.01); *A61B 5/6833* (2013.01); *A61B 5/4528* (2013.01); *A61B 5/4875* (2013.01); *A61B 5/6824* (2013.01); *A61B 2560/0252* (2013.01); *A61B 2562/0204* (2013.01); *A61B 2562/0223* (2013.01); *A61M 1/3656* (2014.02)

(56) References Cited

U.S. PATENT DOCUMENTS

| | | |
|---|---|---|
| 2009/0024041 A1 | 1/2009 | Cho et al. |
| 2009/0215072 A1 | 8/2009 | McDevitt et al. |
| 2012/0053434 A1 | 3/2012 | Saito |
| 2015/0011412 A1 | 1/2015 | Deirmengian et al. |
| 2015/0031049 A1 | 1/2015 | Kentsis et al. |
| 2015/0157262 A1 | 6/2015 | Schuessler |
| 2015/0374245 A1 | 12/2015 | Szilagyi |
| 2016/0112775 A1 | 4/2016 | Kim et al. |
| 2016/0153878 A1 | 6/2016 | Candon et al. |
| 2016/0198961 A1 | 7/2016 | Homyk et al. |
| 2016/0367155 A1 | 12/2016 | Barrett et al. |
| 2017/0055845 A1 | 3/2017 | Mirov et al. |
| 2020/0232983 A1 | 7/2020 | Miller et al. |

FOREIGN PATENT DOCUMENTS

| | | |
|---|---|---|
| WO | WO-2009045374 A2 | 4/2009 |
| WO | WO-2010036930 A1 | 4/2010 |
| WO | WO-2014027293 A2 | 2/2014 |
| WO | WO-2017027643 A1 | 2/2017 |
| WO | 2018183558 | 10/2018 |
| WO | WO-2018183558 A1 | 10/2018 |
| WO | WO-2019055520 A1 | 3/2019 |

OTHER PUBLICATIONS

"International Application Serial No. PCT US2018 024925, Written Opinion dated Jul. 26, 2018", 6 pgs.

"International Application Serial No. PCT/US2018/024925 Written Opinion dated Jul. 26, 2018", 11 pgs.

"International Application Serial No. PCT/US2018/024925, International Search Report dated Jul. 26, 2018", 5 pgs.

EP18775541.8 European Search Report dated Dec. 9, 2020.

PCT/US2018/050675 Search Report dated Nov. 21, 2018.

Schmitt, J. M., Simple photon diffusion analysis of the effects of multiple scattering on pulse oximetry. IEEE Transactions on Biomedical Engineering, vol. 38, No. 12, pp. 1194-1203, 1991.

Schweiger et al. The finite element method for the propagation of light in scattering media: boundary and source conditions. Medical Physics, vol. 22, No. 11, pp. 1779-1792, 1995.

EP18775541.8 European Search Report dated Apr. 1, 2021.

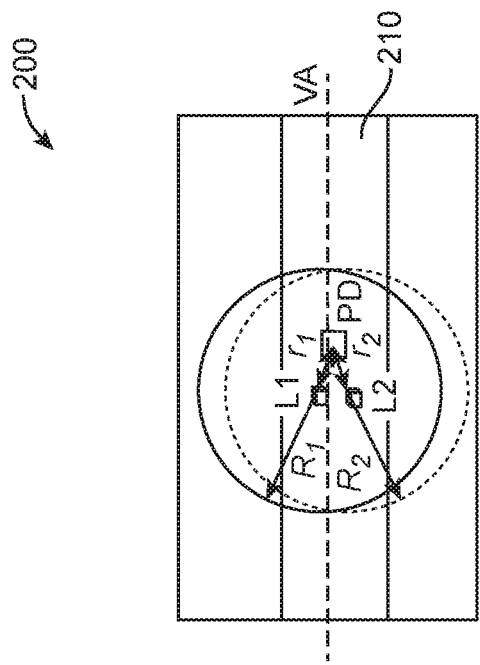
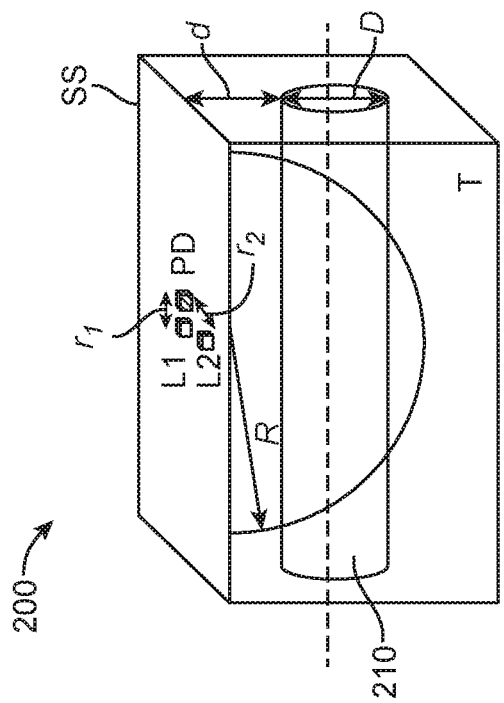

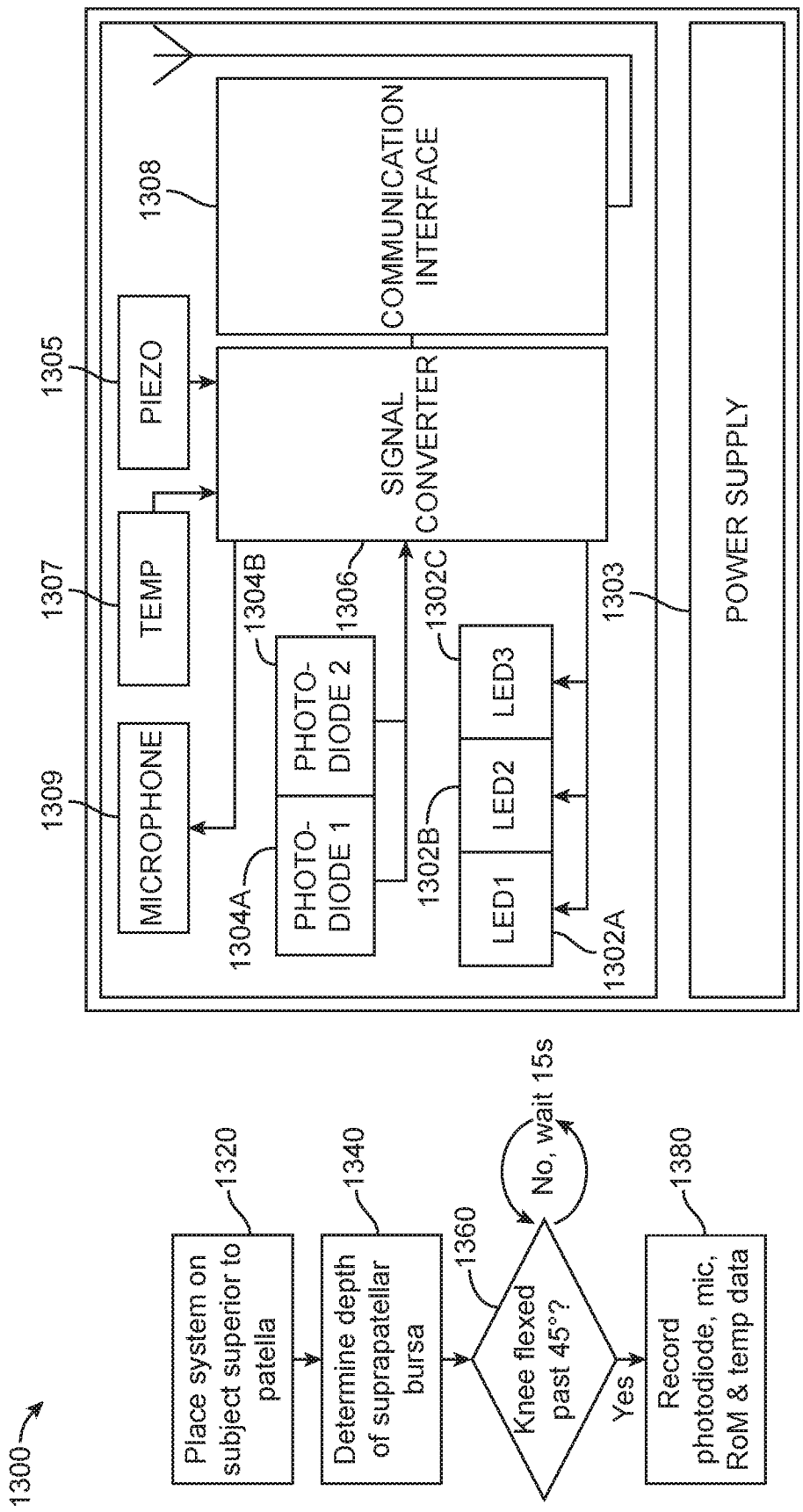

WEARABLE DEVICE WITH MULTIMODAL DIAGNOSTICS

CROSS-REFERENCE TO RELATED APPLICATION

This application is a U.S. National Stage Filing under 35 U.S.C. 371 from International Application No. PCT/US2018/24925, filed on Mar. 28, 2018, which claims the benefit of U.S. Provisional Application No. 62/626,559, filed Feb. 5, 2018, and U.S. Provisional Application No. 62/478,469, filed Mar. 29, 2017, which applications are each incorporated herein by reference.

BACKGROUND OF THE INVENTION

The present disclosure relates to methods and systems using sensors to non-invasively measure subcutaneous processes in a patient. More particularly, the present disclosure relates to systems and methods for measuring one or more fluid properties including systems and methods for measuring one or a plurality of biological fluid properties using optical devices. Additionally, the present disclosure relates to systems and methods for simultaneously measuring a plurality of sensory modalities and processing the measurements to detect physiological phenomenon in the patient's body.

There is a current need for non-invasive techniques to quantitatively measure one or more physiological properties, for example, one or a plurality of biological fluid properties in the physiological environment of the subject or patient, in order to derive clinically relevant metrics to evaluate the state of patients. For example, in dialysis patients there is a current need for measurement of blood and flow related parameters at their dialysis access location, where the parameters include but are not limited to blood hematocrit, hemoglobin concentration, oxygen saturation, heart rate and flow rate, and percentage change in blood volume. Additionally, in total knee arthroplasty (TKA) patients, there is a current need for measurement of parameters relating to, for example, premature implant failure, including synovial fluid white blood cell (WBC) concentration, range of motion, skin temperature, and crepitus associated with a range of disease states.

In an example, stethoscopes are effective tools used in the hospital and doctor's office during physical exams for non-invasive detection of physiologic sounds. Several designs have gained popularity amongst clinicians, such as the Littmann™ stethoscope, and the Welch-Allyn™ stethoscope. These devices have been designed to be portable devices that are clinician-centric and can be easily be moved from one location to another on a patient during a single visit, and also easily used across several patients. Physiological issues such as blocked blood flow, abnormal lung sounds, heart murmurs, etc. occur at specific locations on the body (e.g. the arm for a blocked arteriovenous fistula, the neck for an obstruction in the carotid artery, the chest or back for abnormal air flow in the lungs, etc.) and are typically detectable using stethoscopes during patient-doctor exams. These physiological issues cannot however be effectively tracked outside of the clinic. The stethoscope requires the patient's presence in the clinic to be used by a doctor trained in interpreting the noise heard on the stethoscope. This makes management of patients more difficult and leads to poor patient outcomes, since the patient cannot be monitored for a developing health issue until it has caused the patient damage.

It would be advantageous for noninvasive methods and devices that may be used to monitor physiological phenomenon to allow greater patient mobility. Existing stethoscope designs may hinder patient mobility. These devices are also necessarily rigid due to their underlying architecture. Stethoscopes often have a "cup" or other form of diaphragm that is used to provide acoustic impedance matching from the skin to another medium. These components add to the overall bulk and rigidity of existing stethoscopes. The bulk and rigidity of existing stethoscopes does add to the ease of use for these devices in their classic use case, typically, a clinician moving the stethoscope from one location to another easily to perform a complete physical examination on a patient during their visit. However, this removes them as practical devices that could be used as a long-term, low-profile more portable device for remote monitoring of patient health.

Additionally, the stethoscope is limited to detecting a single sensory modality. The doctor listens for sounds that indicate blocked blood flow, abnormal lung sounds, heart murmurs, for example. The ability to sense more sensory modalities may enable a device to be configured for a wide range of applications. Similarly, techniques that measure biological fluid flow may provide useful diagnostic information to clinicians which may improve patient outcomes.

SUMMARY OF THE INVENTION

Systems and methods of the present disclosure addresses at least some of these needs by providing systems and methods for measuring one or more biological fluid properties using optical devices. The present disclosure enables a non-invasive systems such as an optical system and method to measure one or more physiological properties, such as the properties of biological fluids flowing though, or present in, for example, a vessel or bursa in its physiological environment at a finite depth below the skin surface. Additionally, the present disclosure enables wearable systems and methods for simultaneously measuring one or a plurality of sensory modalities. Such sensory modalities may comprise any one or more of the optical devices disclosed in the present application; however, in alternative embodiments, the systems and methods for simultaneously measuring one or a plurality of sensory modalities may not comprise an optical sensory modality.

In an aspect, an optical detection device is provided. The optical detection device may comprise one or more photodetectors configured to mount on a skin surface of a patient. The one or more photodetectors may be configured to receive light from beneath the skin surface and to generate an electrical signal indicative of the light received. The optical detection device may comprise at least two light sources configured to emit light at different wavelengths and at controllable intensity levels, wherein the light sources are configured to be mounted on the skin surface at variable distances from the photodetector; wherein the light sources may be configured to illuminate the volume of tissue beneath the skin surface, and wherein the photodetector may detect light generated by the light sources and reflected from particles and tissue structure in the illuminated tissue. The optical detection device may comprise a communications interface configured to receive the one or a plurality of electrical signals indicative of intensity from the photodetector and to communicate the one or a plurality of electrical signals to a sensor data processing system, where the intensity of the light received is used to measure one or a plurality of properties of biological fluids flowing in a vessel in the volume of tissue.

Optionally, in any embodiment, the intensity of the light received is used to determine a vessel depth of a fluid vessel in the tissue. Optionally, in any embodiment, the intensity of the light received is used to determine a position of the system relative to the vessel. Optionally, in any embodiment, the intensity of the light received is used to measure one or a plurality of fluid properties inside the vessel. Optionally, in any embodiment, the one or a plurality of fluid properties comprise one or more of: blood oxygenation; heart rate; chemical composition; analyte concentration; cell concentration; leukocyte concentration; erythrocyte concentration; particle concentration; blood flow rate; hematocrit; and hemoglobin concentration.

In another aspect, a method for determining one or a plurality of biological fluid properties from a patient is provided. The method may comprise emitting a first illumination of a volume of tissue below a skin surface of a patient from a first light source a first distance away from a photodetector positioned on the skin surface, where the first light source emits the first illumination at a first intensity to generate a first optical radiation pattern in a first hemispherical volume having a first radius. The method may comprise receiving a first set of electrical signals representing reflection intensities communicated from the photodetector positioned to receive light reflected below the skin surface from the first illumination. The method may comprise emitting a second illumination of the volume of tissue below the skin surface from a second light source a second distance from the photodetector, where the second light source emits the second illumination at a second intensity to generate a second optical radiation pattern in a second hemispherical volume having a second radius. The method may comprise using the first set of electrical signals and the second set of electrical signals to measure one or a plurality of fluid properties of a vessel in the volume of tissue below the skin surface.

Optionally, in any embodiment, the first light source is configured to emit light at a first wavelength and the second light source is configured to emit light at a second wavelength. Optionally, in any embodiment, the step of emitting the first illumination comprises applying a plurality of optical drive signals to the first light source to generate a first plurality of output intensities at the first wavelength. Optionally, in any embodiment, the step of receiving the first set of electrical signals comprises detecting a plurality of reflection intensities for each of the first plurality of output intensities, converting the plurality of reflection intensities to one or a plurality of electrical signals, converting the one or a plurality of electrical signals to digital data values corresponding to the one or a plurality of electrical signals and storing the digital data values of the one or a plurality of electrical signals as the plurality of first wavelength intensities for each of the output intensities in a memory. Optionally, in any embodiment, the step of emitting the second illumination comprises applying the plurality of optical drive signals to the second light source to generate a second plurality of intensities at the second wavelength. Optionally, in any embodiment, the step of receiving the second set of electrical signals comprises detecting a plurality of reflection intensities for each of the second plurality of output intensities, converting the plurality of reflection intensities to one or a plurality of electrical signals, converting the one or a plurality of electrical signals to digital data values corresponding to the one or a plurality of electrical signals, and storing the digital data values of the one or a plurality of electrical signals as the plurality of second wavelength intensities for each of the output intensities in the memory. Optionally, in any embodiment, the step of using the sets of signals to measure one or a plurality of fluid properties comprises determining a plurality of radii for each of the first and second illuminations corresponding to the plurality of first wavelength reflection intensities and the plurality of second wavelength reflection intensities. Optionally, in any embodiment, the step of using the sets of signals to measure one or a plurality of fluid properties comprises determining a depth of a vessel in the volume of tissue illuminated in the steps of emitting based on the plurality of radii at each of the first wavelength and the second wavelength. Optionally, in any embodiment, the step of using the sets of signals to measure one or a plurality of fluid properties comprises determining a diameter of the vessel based on the plurality of radii at each of the first wavelength and the second wavelength.

Optionally, in any embodiment, the method further comprises the first light source configured to emit light at a first at a first wavelength and the second light source configured to emit light at a second wavelength. Optionally, in any embodiment, the step of emitting the first illumination comprises applying a plurality of optical drive signals to the first light source to generate a first plurality of output intensities at the first wavelength. Optionally, in any embodiment, the step of receiving the first set of electrical signals comprises detecting a plurality of reflection intensities for each of the first plurality of output intensities, converting the plurality of reflection intensities to one or a plurality of electrical signals, converting the one or a plurality of electrical signals to digital data values corresponding to the one or a plurality of electrical signals, and storing the digital data values of the one or a plurality of electrical signals as the plurality of first wavelength intensities for each of the output intensities in a memory. Optionally, in any embodiment, the step of emitting the second illumination comprises applying the plurality of optical drive signals to the second light source to generate a second plurality of intensities at the second wavelength. Optionally, in any embodiment, the step of receiving the second set of electrical signals comprises detecting a plurality of reflection intensities for each of the second plurality of output intensities, converting the plurality of reflection intensities to one or a plurality of electrical signals, converting the one or a plurality of electrical signals to digital data values corresponding to the one or a plurality of electrical signals, and storing the digital data values of the one or a plurality of electrical signals as the plurality of second wavelength intensities for each of the output intensities in the memory. Optionally, in any embodiment, the step of using the sets of signals to measure one or a plurality of fluid properties comprises determining a plurality of radii for each of the first and second illuminations corresponding to the plurality of first wavelength reflection intensities and the plurality of second wavelength reflection intensities. Optionally, in any embodiment, the step of using the sets of signals to measure one or a plurality of fluid properties comprises analyzing the plurality of radii for the first illumination to determine a first intersection of the first hemispherical volume of the first optical radiation pattern at each output intensity and the vessel. Optionally, in any embodiment, the step of using the sets of signals to measure one or a plurality of fluid properties comprises analyzing the plurality of radii for the second illumination to determine a second intersection of the second hemispherical volume of the second optical radiation pattern at each output intensity and the vessel. Optionally, in any embodiment, the step of using the sets of signals to measure one or a plurality of fluid properties comprises identifying the first light source as a primary light source when the first intersection is greater than the second intersection and identifying the second light source as the primary light source when the second intersection is greater than the first intersection.

Optionally, in any embodiment, the method further comprises moving the first and second light sources and the photodetector to a location on the skin surface in a direction transverse to the vessel such that the difference between the first intersection and the second intersection is expected to be less when the steps may be repeated after moving the first light source, the second light source, and photodetector.

Optionally, in any embodiment, the method further comprises the first light source configured to emit light at a first wavelength and the second light source configured to emit light at a second wavelength. Optionally, in any embodiment, the method further comprises applying an optical drive signal to the first light source to generate a first output intensity at the first wavelength. Optionally, in any embodiment, the method further comprises receiving a first wavelength reflection intensity for the first output intensity at the first wavelength. Optionally, in any embodiment, the method further comprises storing a digital data value as the first wavelength intensity for the first output intensity in a memory. Optionally, in any embodiment, the method further comprises applying the optical drive signal to the second light source to generate a second output intensity at the second wavelength. Optionally, in any embodiment, the method further comprises receiving a first wavelength reflection intensity for the second output intensity. Optionally, in any embodiment, the method further comprises storing a digital data value as the second wavelength intensity for the second output intensity in the memory. Optionally, in any embodiment, the method further comprises calculating a ratio of reflection intensities by dividing the first wavelength reflection intensity by the second reflection intensity when the first wavelength corresponds to a red light and the second wavelength corresponds to an infrared light, storing the ratio of reflection intensities as corresponding to an oxygenation level of a fluid in the vessel.

Optionally, in any embodiment, the method further comprises the first light source configured to emit light at a first wavelength and the second light source configured to emit light at a second wavelength. Optionally, in any embodiment, the method further comprises periodically performing a measurement for the first light source and the second light source. Optionally, in any embodiment, the periodically performing a measurement comprises applying a plurality of optical drive signals to the first light source to generate a plurality of first output intensities at the first wavelength. Optionally, in any embodiment, the periodically performing a measurement comprises receiving a plurality of first wavelength reflection intensities for each of the first output intensities at the first wavelength. Optionally, in any embodiment, the periodically performing a measurement comprises storing digital data values as the plurality of first wavelength intensity for the first output intensities in a memory. Optionally, in any embodiment, the periodically performing a measurement comprises applying a plurality of optical drive signals to the second light source to generate a plurality of second output intensities at the second wavelength. Optionally, in any embodiment, the periodically performing a measurement comprises receiving a plurality of second wavelength reflection intensities for each of the second output intensities at the second wavelength. Optionally, in any embodiment, the periodically performing a measurement comprises storing digital data values as the plurality of second wavelength intensities for the second output intensities in a memory. Optionally, in any embodiment, the periodically performing a measurement comprises identifying signal artifacts in each of the first wavelength reflection intensities and in each of the second wavelength reflection intensities. Optionally, in any embodiment, the periodically performing a measurement comprises analyzing at each period, the signal artifacts identified in the first wavelength reflection intensities and the second wavelength reflection intensities to determine a period of time between the signal artifacts. Optionally, in any embodiment, the periodically performing a measurement comprises using the period of time between the signal artifacts to determine a heart rate.

In another aspect, a device for sensing information relating to subcutaneous processes in a patient is provided. Optionally, in any embodiment, the wearable device comprises a wearable patch configured to attach to a body part of a patient; a sensor assembly mounted on the wearable patch, the sensor assembly comprising one or more sensors selected from the group consisting of an acoustic sensor, a strain gauge, an optical sensor, a conductivity sensor, a pressure sensor, and an chemical sensor. Optionally, in any embodiment, the wearable device comprises a signal converter configured to receive the one or a plurality of electrical signals from the plurality of sensors and to convert the signals to one or a plurality of sensor data signals comprising a data representation of at least one of the one or a plurality of electrical signals; and a communications interface configured to communicate the one or a plurality of sensor data signals to a sensor data processing system.

Optionally, in any embodiment, the sensor assembly further comprises one or more sensors selected from the group consisting of an accelerometer, a temperature sensor, and a moisture sensor. Optionally, in any embodiment, the sensor assembly comprises one or more of an ultrasonic transducer and an ultrasonic sensor. Optionally, in any embodiment, the sensor assembly comprises an acoustic sensor having a substantially flat sensitivity between about 20 Hz. and about 20 kHz. Optionally, in any embodiment, the sensor assembly comprises an accelerometer having a sensitivity along three axes from 0 Hz. to about 500 Hz. Optionally, in any embodiment, the sensor assembly comprises a strain gauge having a sensitivity to a mechanical strain between about 0.1 Hz. and about 20 Mhz. Optionally, in any embodiment, the sensor assembly comprises a temperature sensor having a resolution below about 0.1° C. Optionally, in any embodiment, the sensor assembly comprises a temperature sensor and the signal converter is configured to sample one or a plurality of electrical signals representing a temperature reading from the temperature sensor at about 8 Hz. Optionally, in any embodiment, the sensor assembly comprises two temperature sensors configured to provide a differential temperature measurement. Optionally, in any embodiment, the sensor assembly comprises one or more of an acoustic sensor and an accelerometer. Optionally, in any embodiment, the acoustic sensor is a piezoelectric device. Optionally, in any embodiment, the piezoelectric device is made of a material selected from any one or more of polyvinylidene fluoride (PVDF), lead zirconate (PZT), a composite including either PVDF or PZT materials. Optionally, in any embodiment, the acoustic sensor is a microphone. Optionally, in any embodiment, the microphone is implemented using a microelectromechanical system. Optionally, in any embodiment, the communication interface comprises a wireless transmitter to transmit the one or a plurality of sensor data signals to the sensor data processing system. Optionally, in any embodiment, the wireless transmitter communicates radio frequency (RF) signals. Optionally, in any embodiment, the radio frequency signals are communicated using a near field communication protocol. Optionally, in any embodiment, the wireless transmitter communicates using a cellular communications system. Optionally, in any embodiment, the wireless transmitter communicates using a wireless local area network system or a near field magnetic communication system.

In another aspect, a system for monitoring a patient is provided. Optionally, in any embodiment, the system comprises a wearable patch configured to attach to a body part of a patient. Optionally, in any embodiment, the wearable patch comprises a sensor assembly comprising a plurality of sensors configured to detect a corresponding plurality of sensory modalities and generate one or a plurality of electrical signals representing the sensory modalities; a signal converter configured to receive the one or a plurality of electrical signals from the plurality of sensors and to convert the signals to one or a plurality of sensor data signals comprising a data representation of at least one of the one or a plurality of electrical signals; a communications interface configured to communicate the one or a plurality of sensor data signals; and a local hub configured to wirelessly receive the one or a plurality of sensor data signals from the wearable patch using a first protocol, and to transmit the one or a plurality of sensor data signals using a second protocol.

Optionally, in any embodiment, the local hub transmits the one or a plurality of sensor data signals to a remote sensor data processor configured to receive the one or a plurality of sensor data signals using the second protocol and to process the one or a plurality of sensor data signals to monitor and alert for thrombosis development or clinically actionable levels of stenosis in a vessel. Optionally, in any embodiment, the first protocol is 2.4 to 2.485 GHz radiofrequency communications protocol, a near field communication protocol, a wireless local area network protocol, or a near field magnetic protocol. Optionally, in any embodiment, the second protocol is a cellular protocol or an Internet protocol. Optionally, in any embodiment, the remote sensor data processor comprises a processor and a storage medium storing computer-executable instructions that when executed are operable to perform phonoangiography using a break frequency to estimate an internal diameter of a carotid artery for the patient. Optionally, in any embodiment, the storage medium stores computer-executable instructions that when executed are operable to determine the break frequency by calculating a frequency power spectrum for a sound measurement and identifying a highest frequency after which a power level drops significantly.

In another aspect, a method for monitoring subcutaneous processes in a patient is provided. Optionally, in any embodiment, the method comprises sensing a plurality of sensory modalities using a sensor assembly comprising one or more sensors mounted on a wearable patch, the one or more sensors selected from the group consisting of an acoustic sensor, a strain gauge, an optical sensor, a conductivity sensor, a temperature sensor, a pressure sensor, and a chemical sensor, where the sensory modalities are received as one or a plurality of electrical signals representing the sensory modalities; converting the one or a plurality of electrical signals to a plurality of corresponding one or a plurality of sensor data signals; and transmitting the one or a plurality of sensor data signals to a sensor data processing system.

Optionally, in any embodiment, the step of sensing the plurality of sensory modalities comprises any one or more of: sensing sound using an acoustic sensor; sensing movement or orientation of a patient body part using an accelerometer; sensing temperature using a temperature sensor; sensing a stretch or compression of the wearable patch using a strain gauge; sensing electromagnetic signals using an optical sensor; sensing moisture using a moisture sensor sensing conductivity using a conductivity sensor; sensing pressure using a pressure sensor; and sensing a chemical using a chemical sensor.

Optionally, in any embodiment, the step of sensing the plurality of sensory modalities comprises sensing a differential measurement of skin temperature from two temperature sensors. Optionally, in any embodiment, the step of transmitting the one or a plurality of sensor data signals to the sensor data processing system comprises: transmitting the one or a plurality of sensor data signals to a local hub, where the local hub transmits the sensor data signal to a remote sensor data processor for processing of the one or a plurality of sensor data signals.

Optionally, in any embodiment, the device can be placed into a shelf mode where power is either disconnected or placed into a low power mode. In some embodiments shelf mode can be automatically entered based on readings from any one or more of: magnetic sensors or switches; optical sensors; motion, acceleration or tilt sensors; temperature sensors; capacitive proximity sensors; and mechanical switches. Optionally, in any embodiment, shelf mode can invoked by a microcontroller device and exited based on readings from any one or more of: magnetic sensors or switches; optical sensors; motion, acceleration or tilt sensors; temperature sensors; capacitive proximity sensors; and mechanical switches.

Optionally, in any embodiment, the above sensors interact with product packaging or an adhesive backing liner in order to exit shelf mode when the patch is removed from the product packaging. Optionally, in any embodiment, the device can be placed into a shelf mode where power is either disconnected or placed into low power modes. Optionally, in any embodiment, shelf mode is either invoked by a microcontroller device or automatically entered, based on readings from any one or more of magnetic sensors or switches; optical sensors; motion, acceleration or tilt sensors; temperature sensors; capacitive proximity sensors; and mechanical switches. Optionally, in any embodiment, shelf mode can be invoked by a microcontroller device and exited based on readings from any one or more of: magnetic sensors or switches; optical sensors; motion, acceleration or tilt sensors; temperature sensors; capacitive proximity sensors; and mechanical switches. Optionally, in any embodiment, the above sensors interact with product packaging or an adhesive backing liner in order to exit shelf mode when the patch is removed from the product packaging.

Optionally, in any embodiment, the device can be placed into a shelf mode where power is either disconnected or placed into a low power mode. Optionally, in any embodiment, shelf mode is either invoked by a microcontroller device or automatically entered, based on readings from any one or more of: magnetic sensors or switches; optical sensors; motion, acceleration or tilt sensors; temperature sensors; capacitive proximity sensors; and mechanical switches. Optionally, in any embodiment, shelf mode can invoked by a microcontroller device and exited based on readings from any one or more of: magnetic sensors or switches; optical sensors; motion, acceleration or tilt sensors; temperature sensors; capacitive proximity sensors; and mechanical switches. Optionally, in any embodiment, the above sensors interact with product packaging or an adhesive backing liner in order to exit shelf mode when the patch is removed from the product packaging.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIGS. 2A and 2B are an isometric and a top view, respectively, of an example of an optical measuring system for measuring one or a plurality of biological fluid properties in the system in FIG. 1;

FIG. 13A is a flow chart illustrating operation of the system in FIGS. 2A and 2B positioned on a skin surface superior to the patella of a patient;

FIG. 13B is a block diagram of an example of a system for measuring one or a plurality of biological fluid properties from an optical sensor on a skin surface superior to the patella of a patient;

DETAILED DESCRIPTION OF THE INVENTION

I. Optical Detection of Biological Fluid Properties
I. System Overview

Disclosed herein are systems and methods for measuring one or a plurality of biological fluid properties from a patient's body. Examples of systems comprise an optical system comprising at least two light sources, at least one photodetector, and data processing resources for analyzing the data collected using the light sources and photodetector. The light sources are identified as light-emitting diodes (LEDs) throughout this description, however, any suitable light source with a controllable intensity and in some implementations, different wavelengths, may be used as well. The LEDs are controlled to illuminate a region in the tissue below the LEDs. The photodetector senses light reflected from, or transmitted through, the tissue below the LEDs and generates a current corresponding to the intensity of the reflected light. The distances between the LEDs and photodetector are known and the position of each LED relative to each other, to the photodetector, and to any fluid vessels below the skin surface is also known.

Any number of LEDs may be used in the system depending on the measurements to be taken and the sensitivity desired. The different LEDs may be needed for emitting light at different wavelengths, or for illuminating the tissue from different positions on the skin surface. Multiple photodetectors may be used as well to measure intensities at different wavelengths, or at different positions on the skin surface.

Figure 1:
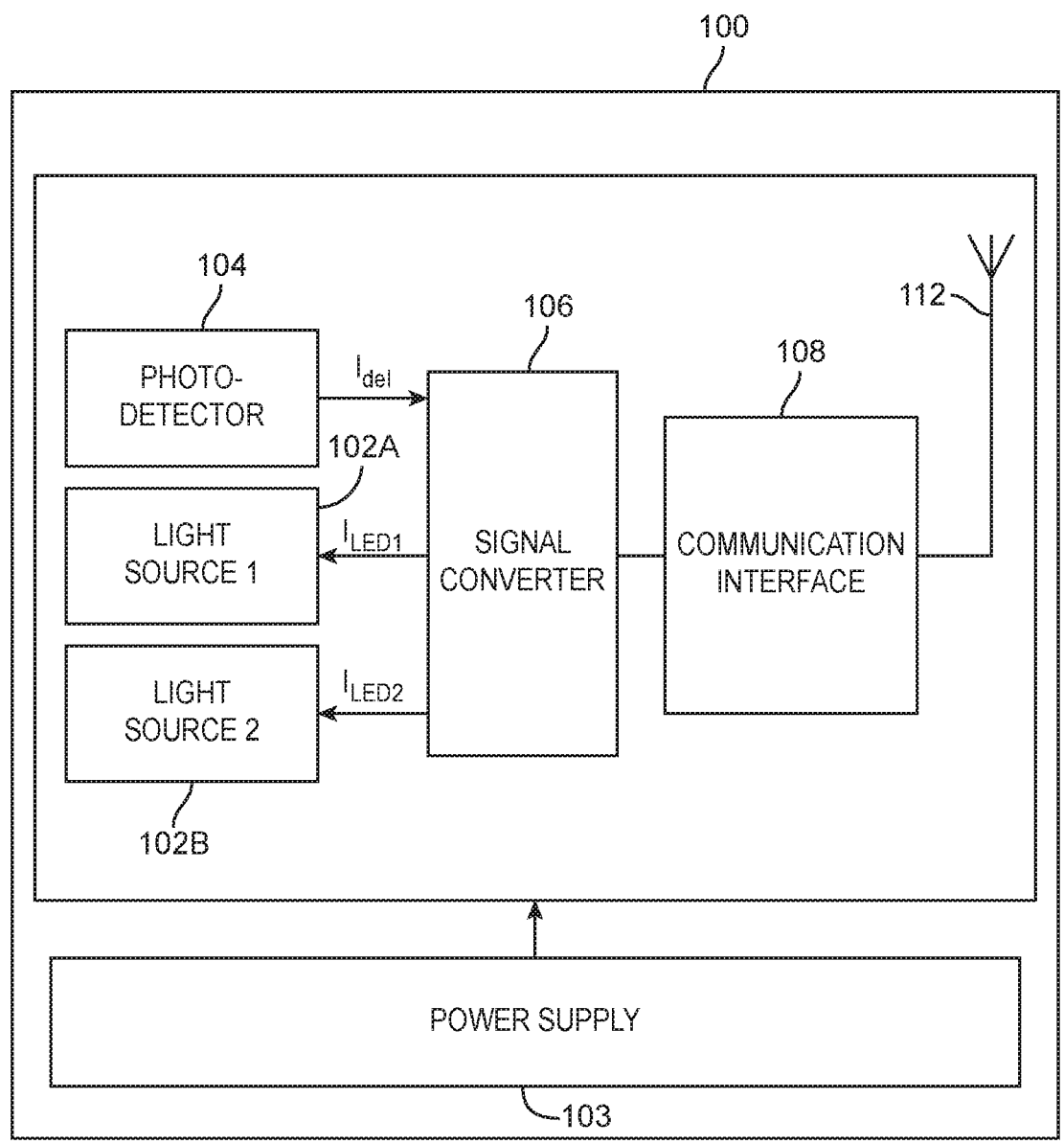
FIG. 1 is a block diagram of an example of a system for measuring biological one or a plurality of fluid properties.

FIG. 1 is an example of a system 100 for measuring biological fluid vessel properties. The system 100 in FIG. 1 comprises at least two light sources (LEDs in the described example) 102a, 102b, a photodetector 104, a signal converter 106, and a communication interface 108. The LEDs 102, the photodetector 104, the signal converter 106, and communications interface 108 may be mounted in or on a casing, substrate or other holding structure in a manner that allows each LED 102a, 102b to contact the patient's skin S. The casing or substrate may be any suitable structure. In one example implementation, the LEDs 102 and the photodetector 104 are disposed on a flexible, stretchable substrate formed as a type of patch with an adhesive that would allow the patient to wear the system for constant monitoring. The stretchable substrate, for example extended polytetrafluoroethylene (ePTFE), enables a wider range of adherent form factors, including on or near articulating joints. The substrate contains corrugated traces that allow the device to stretch without disrupting electrical connections. These traces may be placed by a physical vapor deposition process when the substrate is at maximum stretch. Rigid and flexible electronics components can then be assembled on the deposited traces using, for instance, a reflow soldering process. This can be done either while the substrate is still at stretch or after it has reverted to its resting dimensions. Where the substrate is ePTFE, the device is able to dynamically stretch by more than 20% of its total length, even when populated by rigid electronics components, due to the material's ability to stretch by ~50% when unpopulated.

The LEDs 102a, 102b are mounted in the structure so as to contact the skin to irradiate the tissue below the skin with a light having an intensity controlled by a current level. Each LED 102a, 102b is driven to illuminate the tissue by a corresponding current $I_{LED1}$ and $I_{LED2}$, respectively. The system in FIG. 1 depicts two LEDs, however, additional LEDs may be used.

The photodetector 104 is also mounted on the skin to receive reflectance values corresponding to light reflected from scattering off the structure in the tissue beneath the skin. The photodetector 104 detects the light and emits a current, $I_{det}$, corresponding to the intensity of the reflected light. One photodetector 104 is used in the system 100 in FIG. 1. In other examples, additional photodetectors may be used.

The signal converter 106 and communications interface 108 are optional and represent a connection by Which reflectance values may be communicated to a processing system for analysis. A simple hardwired connection may be used to connect the system to a processing system. The signal converter 106 and communications interface 108 allow for the system 100 to be implemented on a wearable patch to allow for remote monitoring of the patient. The signal converter 106 may modulate or encode a signal to be communicated to a processing system. The communications interface 108 may then communicate the signal wirelessly via antenna 112.

The system 100 may receive power from a power supply 103, which may be a simple battery. The power supply may comprise a wakeup sensor to trigger the power supply 103 to start the system 100 when the system 100 is moved from a storage state to an operable state. The wakeup sensor may for example be implemented as a magnetic sensor that keeps the power off in proximity to a magnetized packaging, but then triggers the power on when moved away from the magnetized packaging. The wakeup sensor may also be a piezoelectric film that remains in a quiescent state until it is stretched, inducing a voltage to activate the device. Other modalities may be used for the wakeup sensor such as light or pressure.

FIGS. 2A and 2B are an isometric and a top view, respectively, of an example of an optical measuring system 200 for measuring biological fluid properties in the system in FIG. 1. The system 200 in FIGS. 2A and 2B comprises two LEDs L1, L2 and one photodetector PD (housing not shown). Additional LEDs or photodetectors may be used. FIGS. 2A and 2B shows the position of each component on the skin relative to a biological fluid carrying vessel 210 with a diameter, D, at a finite depth, d, in the tissue T below the skin surface S. The LEDs L1, L2, each emit corresponding optical radiation patterns to illuminate the tissue. The optical radiation patterns are illustrated in FIGS. 2A and 2B as two separate hemispherical volumes (in FIGS. 2A and 2B, L1 generates an optical radiation pattern shown as a hemispherical volume with radius $R_1$ and L2 generates an optical radiation pattern shown as a hemispherical volume with radius $R_2$). The LEDS, L1, L2, may be selected to emit at different wavelengths, such as for example, green, yellow, red, infrared (IR), or other wavelengths.

The two LEDs L1, L2 are shown to be located at a center-to-center distance of $r_1$, $r_2$ from the photodetector and placed along the axis of the vessel 210. The hemispherical volumes representing the optical radiation patterns are depicted as each having a radius $R_1$ and $R_2$ for L1, L2 respectively. The radius $R_1$, $R_2$ of the optical radiation pattern is dependent on the light wavelength and the corresponding absorption and scattering properties of the tissue and its constituents at the wavelength. It is noted that the system 100 in FIG. 1 is one of many example implementations and its description herein is not intended to limit the many possible implementations that are feasible to achieve the intended function of the system. The example system 200 in FIGS. 24 and 2B implements a minimum two LEDs located at a known distance from at least one photodetector. While the system is functional with two LEDs and one photodetector, more LEDs and photodetectors can be used to increase the measurement performance as detailed in the description below.

FIGS. 3A, 3B, 4A, and 4B below illustrate how the system in FIGS. 1, 2A, and 2B may be used to obtain different measurements of properties of biological fluid vessels. The system may be modified in various ways as described below by using more than two LEDs or by using LEDs with different wavelengths. It is to be understood that the descriptions below are not intended as limiting the system to any one implementation.

2. Measurement Techniques

Measuring the Depth of the Fluid Vessel Below the Skin Surface

Figure 3B:
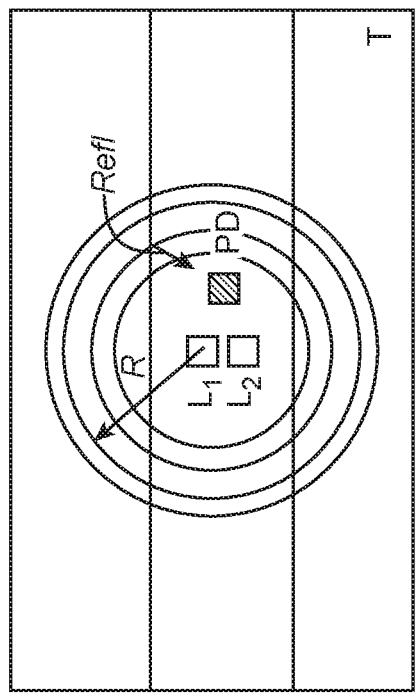
FIGS. 3A and 3B are a side and a top view, respectively, of an example of the optical measuring system of FIGS. 2A and 2B used for measuring the depth of biological fluid carrying vessels below the skin surface.
Figure 3A:
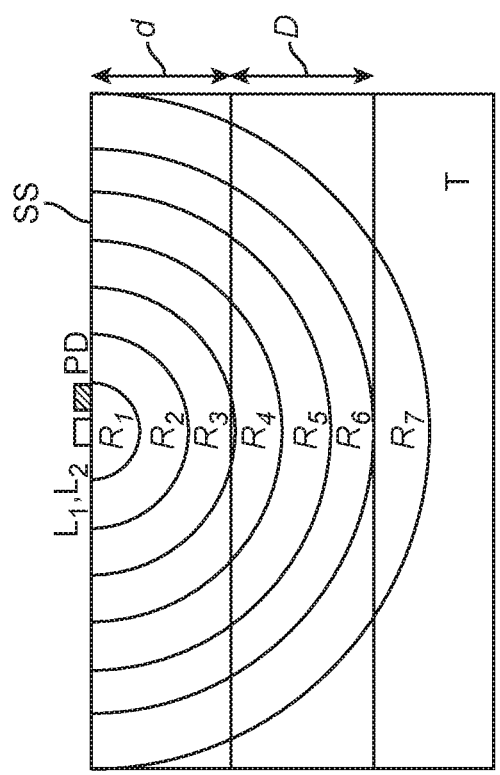

FIGS. 3A and 3B are a side and a top view, respectively, of an example of the optical measuring system of FIGS. 2A and 2B used for measuring the depth of biological fluid carrying vessels below the skin surface. In FIG. 3A, the side view depicts the optical radiation pattern in the tissue induced by one of the at least two LEDs L1, L2 portrayed as a series of hemispherical volumes with increasing radii R1, R2, R3, R4, R5, R6 and R7 corresponding to increasing light intensity. FIG. 3B depicts the same radiation pattern from the top, alongside the photodetector PD with the hemispherical pattern centered about LED L1 for illustration purposes.

Each of the at least two LEDs can enable emission of light at increasing intensities by increasing the power, via the current $I_{LED}$, supplied to the LEDs. As shown in FIGS. 3A and 3B, light emitted into the tissue undergoes absorption and scattering due to the tissue and its constituents. The absorption and scattering is depicted in FIGS. 3A and 3B by the hemispherical optical radiation pattern with radius R, and a portion of this light (arrow Refl) is scattered back into the photodetector, thus enabling the measurement of optical reflectance characteristics within this region of influence. An increase in light intensity results in the light emitted in the tissue to penetrate deeper, and consequently, enable the measurement of optical reflectance characteristics within regions of influence that are increasing in size, corresponding to hemispherical radiation volumes with increasing radii R1, R2, R3, R4, R5, R6 and R7 centered about the position of the LED. This enables a spatial, depth-based optical reflectance measurement of the biological fluid carrying vessel at a finite depth in the tissue. Changes observed in the optical reflectance measurement with increasing light intensity, and consequently increasing radiation volume radius, can be used to determine the depth, d (from R3 to R4), and diameter, D (from R6 to R7), of the vessel.

One example method for determining the depth of a vessel comprises the steps of:
 a. generating a light from a first light source positioned on a skin surface above a fluid vessel at each of a plurality of intensity levels, each intensity level corresponding to a radius of a hemispherical region of influence;
 b. measuring a first plurality of reflectance values each corresponding to each of the plurality of intensity levels of the first light;
 c. generating a light from a second light source positioned on the skin surface proximal to the first light source at each of the plurality of intensity levels;
 d. measuring a second plurality of reflectance values corresponding to each of the plurality of intensity levels;
 e. determining a vessel depth and a vessel diameter from changes in reflectance values with increasing light intensity.

The techniques described above may be used to determine the optical intensity required to 'meaningfully' irradiate and sense the region of the vessel below the LED L1 (R7 in FIG. 3A).

Detection of the Position of the System Over the Fluid Vessel

Figure 4B:
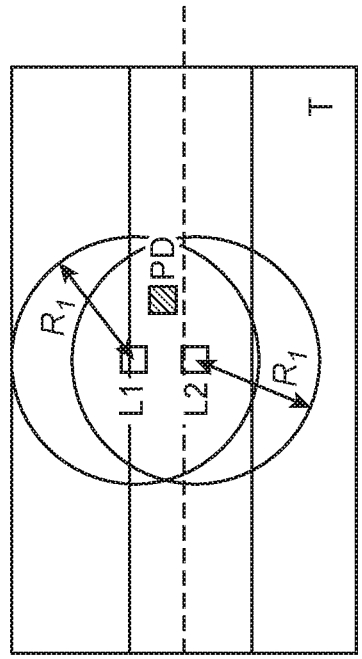
FIGS. 4A and 4B are a top view centered and a top view off-axis, respectively, of an example of the optical measuring system of FIGS. 2A and 2B used for determining a position of the system relative to the biological fluid carrying vessels below the skin surface.
Figure 4A:
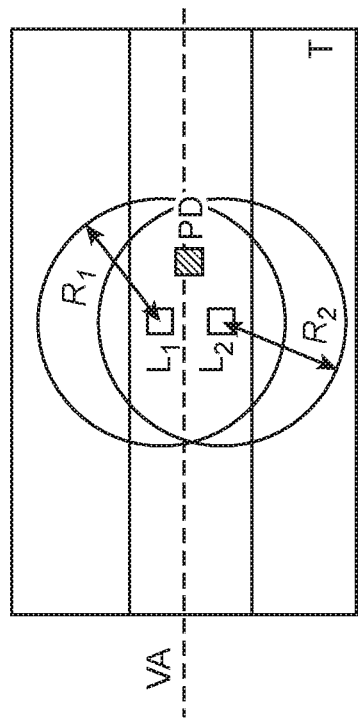

FIGS. 4A and 4B are a first top view and a second top view of an example of the optical measuring system of FIGS. 2A and 2B used for determining a position of the system relative to the biological fluid carrying vessels below the skin surface. In FIG. 4A, the top view depicts the two LEDs L1, L2 and photodetector Pt) centered about the vessel axis VA with their corresponding optical radiation patterns induced in the tissue portrayed as two separate hemispherical volumes (L1 & L2). In FIG. 4B, the second top view depicts the same radiation patterns but with the two LEDs L1, L2 and photodetector PD offset with respect to the vessel axis VA.

The two LEDs L1, L2 and the photodetector PD enable the measurement of the tissue's optical reflectance characteristics within a region of influence corresponding to the LED's optical radiation pattern centered about the position of the LEDs (see FIG. 4A, L1 generates a first radiation pattern, and L2 generates a second radiation pattern). The light intensity of each LED can be independently adjusted to irradiate the region below the LEDs with their respective optical radiation pattern radii intersecting the vessel (see R4 to R7 in FIG. 3A). The system as shown in FIGS. 4A and 4B enables a two-point, spatial measurement of the optical reflectance characteristics of the biological fluid carrying vessel at a finite depth in the tissue. The relative level of signal strength of the optical reflectance measurement at the photodetector PD due to light from LEDs L1 and L2 can be used to determine the relative position of the system over the vessel. For example, FIGS. 4A and 4B depicts two cases, centered and off-axis, respectively. A scan of different light intensities at each LED, L1 and L2 would result in a set of reflectance values corresponding to each LED that provide a data pattern corresponding to the intersection of the fluid vessel and the two hemispherical irradiation volumes. The data pattern for the LEDs in the case in which the LEDs, L1 and L2, centered would be substantially the same. The data pattern for the LEDs in the case in which the LEDs are off-axis would be different. The differences in the data patterns in the off-axis case would make it possible to determine which LED is the primary LED light source for use in biological fluid properties or flow measurements inside the vessel. The LED for which the intersection of the hemispherical irradiation volume and vessel is maximized (such as for example, LED L2 in FIGS. 4A and 4B) would be deemed the primary LED. If it is desired to center the LEDs and the photodetector over the vessel, the LEDs and photodetector can be moved in a direction transverse to the vessel such that the intersection of the irradiation volume and vessel is more equal for each LED. The process may be repeated until a substantially centered system over the vessel is achieved.

Measurement of Fluid Properties Including Particle Concentration and Flow Rate Inside a Vessel Referring to FIGS. 2A and 2B, the two LEDs L1, L2 and photodetector PD in the system 200 enable the measurement of the tissue's optical reflectance characteristics within a region of influence corresponding to the LED's optical radiation pattern centered about the position of the LED (see FIGS. 4A and 4B, LED L1 generates a radiation pattern with radius r1 and the LED L2 generates a radiation pattern with radius r2). The optical light intensity of the LEDs can be adjusted to irradiate the region below the LEDs with their respective optical radiation pattern radii reaching beyond the bottom of the vessel (R>d+D, see R7 in FIG. 3A), The LEDs L1, L2 may be configured to emit light at two different optical wavelengths $\lambda 1$, $\lambda 2$. This enables a two-wavelength measurement of the optical reflectance characteristics of the biological fluid in the vessel, where the fluid exhibits different optical absorption and scattering characteristics at the two wavelengths. The relative level of signal strength of the optical reflectance measurement at the photodetector PD due to light at the two wavelengths $\lambda 1$, $\lambda 2$ (from LEDs L1 and L2) can be used to determine the one or a plurality of properties of the biological fluid. The one or a plurality of properties that may be determined include, but are not limited to, chemical composition and analyte concentration, particularly where the analyte is a specific type of cell.

In one example implementation, one LED that can emit light in the infrared and one LED that can emit red light may be used to measure oxygenation levels in blood flowing through the vessel. For example, the oxygenation levels may be measured by calculating the ratio of optical reflectance measured at the two wavelengths. In addition, the frequency of repetitive signal artifacts observed in the optical reflectance measured at one or more wavelengths may also be analyzed allowing for the determination of the heart rate. While the system may be implemented with two LEDs at different wavelengths and one photodetector, a more robust system may comprise additional LEDs or wavelengths and photodetectors that can be used to increase the measurement performance. For example, the use of an additional LED that emits light at green wavelength can provide an improved heart rate measurement by sensing the blood flowing through the vessel.

In another example implementation, one LED that can emit light in the infrared and one LED that can emit yellow light may be used to measure the white blood cell (WBC) concentration in the synovial fluid in a subcutaneous bursa. For example, the WBC concentration may be measured by calculating the ratio of optical reflectance and/or transmittance measured at the two wavelengths by at least one, but possibly more, photodetectors.

3. Model of System and Tissue interaction

The feasibility and strength of the measurement techniques described above may be validated by modeling the system and tissue interaction using analytical and finite element method (FEM) formulations. The modeling also informs the system parameters (including but not limited to components and their related control parameters) that may be adjusted to achieve the intended function of measuring one or a plurality of properties of biological fluids flowing through, or present in, a vessel or a bursa in its physiological environment at a finite depth below the skin surface. These system parameters comprise but are not limited to optimal number of LEDs, number of photodetectors (PD), light wavelengths, LED light intensity, and LED & PD spacings and position.

Model Objectives:

The main objective of the analytical formulation is to quantitatively model the LED light source L and the optical absorption and scattering experienced by the light in the tissue, in order to determine the optical reflectance measured at the photodetector. The fundamental theory behind the formulation is particle diffusion, wherein light is treated as a particle which undergoes absorption and scattering in the tissue depending on the optical properties.

Figure 5:
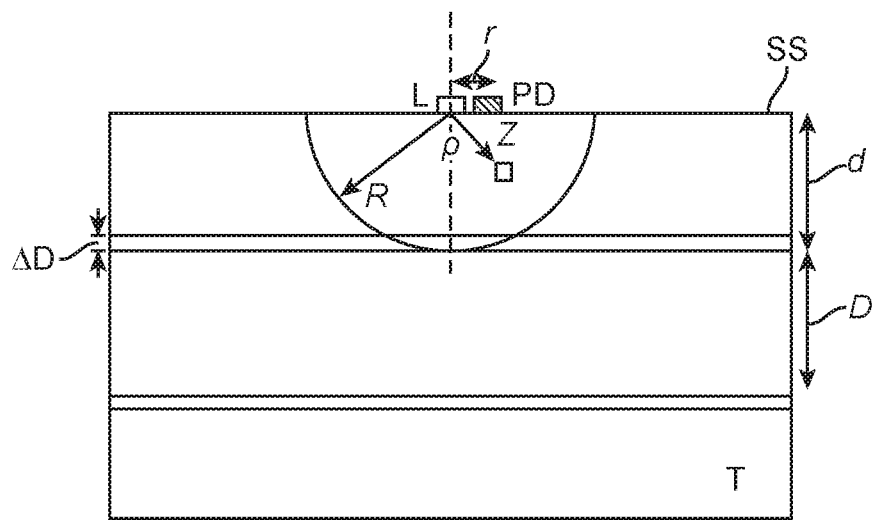
FIGS. 5 and 6 are side views of an example of the optical system of FIGS. 2A and 2B illustrating use of an analytical model for determining and analyzing optical reflectance data in measuring one or a plurality of biological fluid properties.

Model Formulation:

FIG. 5 is a side view depicting the cross-section of the optical radiation pattern in the tissue T induced by one of the at least two LEDs L, where the optical radiation pattern is represented as a hemispherical volume with radius R; Parameters defined for the analytical model include:
1. L-PD spacing r,
2. random tissue voxel position ($\rho$, z),
3. vessel depth d and diameter D,
4. vessel radial dilation about its axis during pulsatile fluid flow $\Delta D$.

By using particle diffusion theory[1], the following analytical expression can be derived for the steady-state (DC) photon flux at a random tissue voxel position ($\rho$, z):

[1] J. M. Schmitt, "Simple Photon Diffusion Analysis of the Effects of Multiple Scattering on Pulse Oximetry," IEEE Transactions on Biomedical Engineering, vol. 38, no. 12, December 1991. (incorporated by reference)

$$\psi_{dc}(\rho) = \frac{P}{\mu_s 2\pi \rho^2}\left[C_1 e^{-\alpha\rho}\left(\frac{1}{\rho} + \alpha\right) + C_2 e^{\alpha\rho}\left(\frac{1}{\rho} - \alpha\right)\right]$$

where,
$\psi$—Photon flux
P—Optical power emitted by the LED
$\mu_a$—absorption coefficient of tissue
$\mu_s$—transport-corrected scattering coefficient of tissue $\alpha = \sqrt{3\mu_a\mu_s}$ C1, C2—constants that are calculated depending on the boundary conditions (BC) at the hemispherical optical radiation volume (BC1: $\rho$=r, z=R) and LED (BC2: $\rho$=0, z=0).

For Boundary Condition BC1: As shown in FIG. 5, the optical absorption and scattering phenomena encountered by the light is expected to differ at the tissue-vessel boundary (R=d) depending on the absorption ($\mu_a^b$) and scattering ($\mu_s^b$) coefficients of the fluid relative to that of the tissue. This boundary can be modeled using a Robin-type boundary condition 2:

[2] M. Schweiger et al., "The Finite element method for the propagation of light in scattering media: Boundary and source conditions," Medical Physics, vol. 22, no. 11, pt. 1, November 1995.

$$\text{Photon flux } \psi(\rho) + 2k_b \frac{d\psi(\rho)}{d\rho} = 0 \text{ at } \rho = R$$

where, the diffusion coefficient in fluid is $$k_b = \frac{1}{3(\mu_a^b + \mu_s^b)}.$$

For boundary condition BC2—the flux density at the LED can be defined as:

$$\lim_{\rho \to 0}\left[-4\pi k\rho^2 \frac{d\psi(\rho)}{d\rho}\right] = P$$

By applying boundary conditions BC1 and BC2 to the steady-state photon flux, C1 and C2 can be determined:

$$C_1 = \frac{1}{(1 - e^{-2\alpha R})}\left(1 - \frac{2k_b}{R} + 2k_b\alpha\right)$$

$$C_2 = \frac{1}{(1 - e^{2\alpha R})}\left(1 - \frac{2k_b}{R} - 2k_b\alpha\right)$$

The steady state current ($I_{dc}$) due to the optical reflectance from the tissue measured at the photodetector, with an area $PD_{area}$ and conversion factor at the specific LED wavelength, spectral sensitivity SS, can be defined as:

$$I_{dc} = PD_{area} \times SS \times \psi_{dc}(\rho = r)$$

$$= PD_{area} SS \frac{P}{\mu_s 2\pi r^2}\left[C_1 e^{-\alpha r}\left(\frac{1}{r} + \alpha\right) + C_2 e^{\alpha r}\left(\frac{1}{r} - \alpha\right)\right]$$

Figure 6:
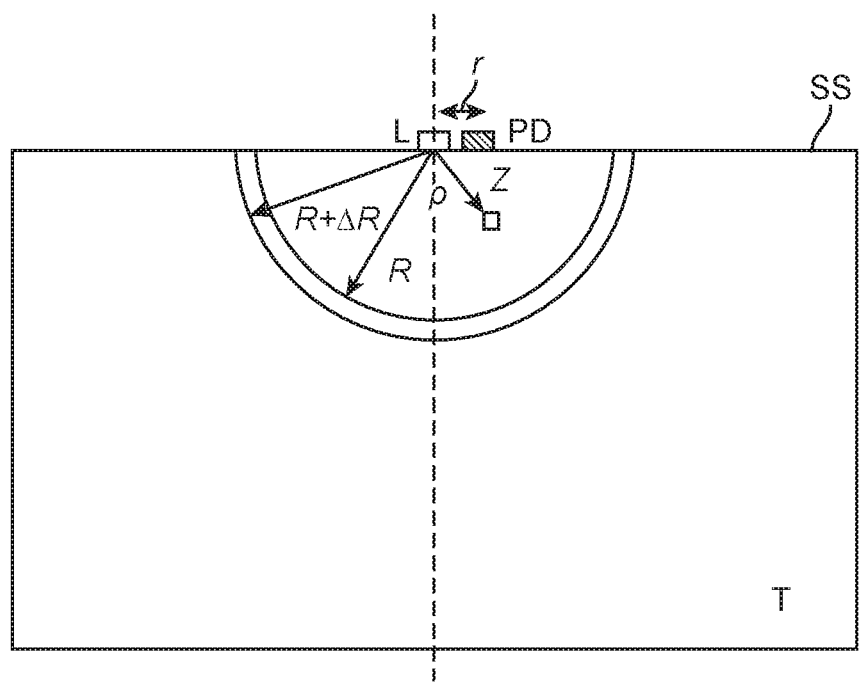

FIG. 6 is an example of the system as shown in FIG. 5, where the vessel radial dilation about its axis during pulsatile fluid flow $\Delta D$ is approximated by an increase in the hemispherical optical radiation pattern radius by dR, which physically constitutes the increase in fluid corresponding to the pulsatile dilation of the vessel.

The pulsatile fluid flow in the vessel manifests itself as a radial vessel dilation $\Delta D$ about its axis as depicted in FIG. 5. In order to investigate the time-varying photodetector current ($I_{ac}$) during pulsatile fluid flow, the increase in fluid corresponding to the pulsatile dilation of the vessel is approximated by an increase in the hemispherical optical radiation pattern radius by $\Delta R$ (see FIG. 6). With this approximation, the time-varying photodetector current ($I_{ac}$) can be defined as:

$$I_{ac} = \Delta R \frac{dI_{dc}}{dR} = \Delta R \, PD_{area} SS \frac{\alpha P}{\mu_s \pi r^2} \left[ \left( e^{-2\alpha R} C_1 - \frac{k_b}{\alpha R^2} \right) \frac{e^{-\alpha r}}{1-e^{-2\alpha R}} \left( \frac{1}{r} + \alpha \right) - \left( e^{2\alpha R} C_2 + \frac{k_b}{\alpha R^2} \right) \frac{e^{\alpha r}}{1-e^{2\alpha R}} \left( \frac{1}{r} - \alpha \right) \right]$$

Measurement of Biological Fluid Carrying Vessel Depth Below Skin Surface:

A technique for measuring the depth of a vessel below the skin surface on which the system is positioned was described above with reference to FIGS. 3A and 3B. One way to simplify the technique and to enable the measurement of one or a plurality of properties of biological fluids flowing through the vessel (having a diameter, D) in its physiological environment at a finite depth, d, below the skin surface, is to ascertain the minimum, threshold optical light intensity or LED current $I_{LEDth}$. The minimum, threshold optical light intensity current, $I_{LEDth}$, is the level of current needed to drive the LED in order to irradiate the region below the LEDs and for the respective optical radiation pattern radii of the LEDs to reach the vessel (R>d, see R3 in FIGS. 3A and 3B). Irradiating the tissue to a sufficient depth enables vessel depth measurement.

The $I_{LEDth}$ operating point may be determined using the analytical model used to analyze the measured data by calibrating it to the photodetector technical specifications, including but not limited to the minimum detectable current, $I_{PDmin}$ and the maximum usable current, $I_{PDmax}$. In addition, the measured photodetector DC current $I_{dc}$ at increasing LED power can be used to further calibrate the model for the subject's tissue characteristics.

$$I_{det}(I_{LED}) = \frac{I_{ac}(I_{LED})}{I_{dc}(I_{LED})} - \frac{I_{PDmin}}{I_{dc}(I_{LED})}$$

where, $$I_{det}(I_{LED}) > \frac{I_{PDmin}}{I_{PDmax}}$$

can be used to determine the minimum, threshold LED current $I_{LEDth}$ needed to reach the vessel.

Figure 7:
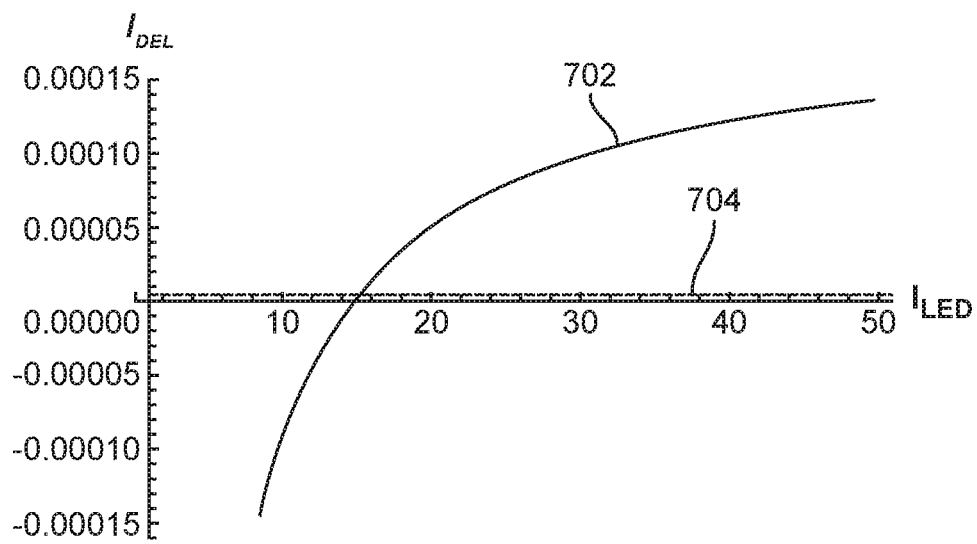
FIG. 7 is a graph illustrating a determination of a minimum threshold LED current to illuminate the tissue sufficiently to reach the vessel.

FIG. 7 is a graph illustrating how a minimum threshold LED current to illuminate the tissue sufficiently to reach the vessel may be determined. The LEDs may then be energized at a range of currents while measuring and calculating $I_{det}(I_{LED})$ 702 and $$\frac{I_{PDmin}}{I_{PDmax}}$$

704. The $I_{det}(I_{LED})$ 702 and $$\frac{I_{PDmin}}{I_{PDmax}}$$

704 are plotted as a function of $I_{LED}$ as shown in FIG. 7. The point of intersection of the $I_{det}(I_{LED})$ plot and the $$\frac{I_{PDmin}}{I_{PDmax}}$$

plot indicates the minimum, threshold LED current $I_{LEDth}$ needed to reach the vessel.

Figure 8:
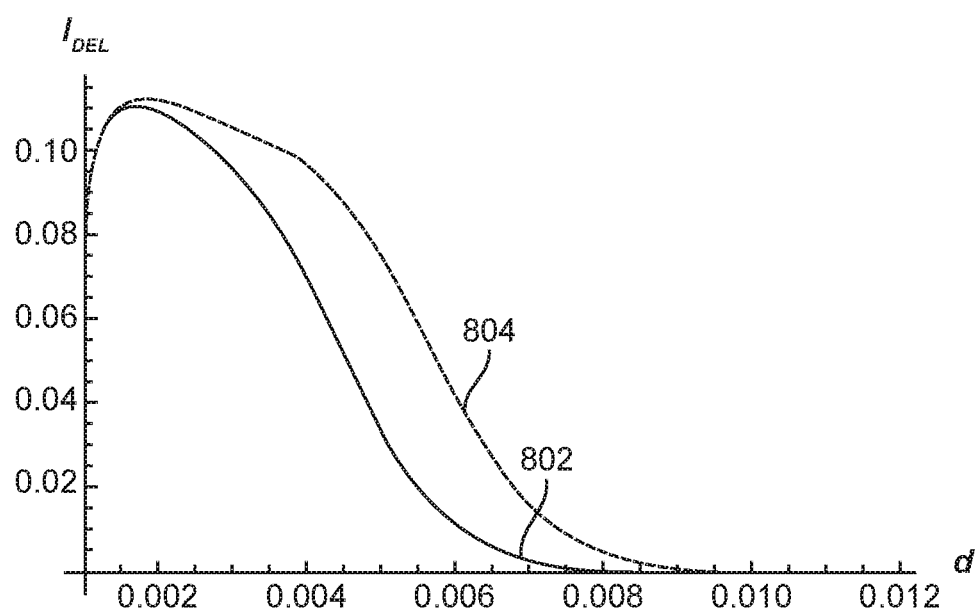
FIG. 8 is a graph of current at the photodetector, $I_{det}$, as a function of the depth, d, of the fluid vessel for different LED to photodetector spacings.

FIG. 8 is a graph of current at the photodetector, $I_{det}$, as a function of the depth, d, of the fluid vessel for different LED-to-photodetector spacings. FIG. 8 shows an example plot of $I_{det}$ with LED-PD spacing of $r_1=5.3$ mm, 802, and FIG. 8 also shows an example plot of $I_{det}$ with LED-PD spacing of $r_2=6.5$, 804. FIG. 8 shows the system can be appropriately configured to be sensitive to vessels with varying depths by adjusting the LED to photodetector center-to-center spacing r (see FIGS. 2A and 2B). As shown in FIG. 8, the analytical model predicts that the system sensitivity to deeper vessels increases as the LED-PD spacing r increases.

4. Biological Fluid Property Measurement Inside Vessel:

In order to enable the measurement of one or a plurality of properties of biological fluids flowing through a vessel (diameter D) in its physiological environment at a finite depth d below the skin surface, in addition the minimum, threshold optical light intensity or LED current $I_{LEDth}$ needed to reach the vessel, one needs to be able to ascertain the optimal optical light intensity or LED current $I_{LEDopt}$ needed to irradiate the region below the LEDs and their respective optical radiation pattern radii to reach beyond the bottom of the vessel (R>d+D, see $R_7$ in FIGS. 2A and 2B). This operating point can be determined empirically by detecting an inflection point in $I_{det}(I_{LED})$ by sweeping $I_{LED}$ after crossing the threshold LED current $I_{LEDth}$.

Once this inflection point is found for the at least two LEDs L1, L2, the optimal LED current $I_{LEDopt}$ can be determined for each of the at least two LEDs in the system and this operating point maintained when performing biological fluid property measurement inside the vessel. For example, the at least two LEDs L1, L2 can be designed to emit light at two different optical wavelengths $\lambda_1, \lambda_2$. The relative level of signal strength of the optical reflectance measurement at the photodetector i.e.

$$\frac{I_{det}[L1]}{I_{det}[L2]}$$

can be used to determine the one or a plurality of properties of the biological fluid. These properties comprise but are not limited to chemical composition and analyte concentration. One envisioned embodiment of this invention is the use of two LEDs that can emit light at infrared and red wavelengths to measure oxygenation levels in blood flowing through the vessel, by calculating the ratio of optical reflectance measured at the two wavelengths. Further, by analyzing the frequency of the repetitive signal artifacts observed in the optical reflectance measured at one or more wavelengths, the heart rate can be determined.

Particle Concentration and Flow Rate of the Biological Fluid:

In order to measure the particle concentration and flow rate of the biological fluid in the vessel, the LEDs L1, L2 can be configured to emit light at the same optical wavelength, but located at different center-to-center spacing from the photodetector $r_1, r_2$. Following the determination and setting of the operating point, i.e. the optimal LED current $I_{LEDopt}$ for each of the at least two LEDs L1, L2, the relative level of signal strength of the optical reflectance measurement at the photodetector, i.e.

$$R = \frac{I_{det}[L1]}{I_{det}[L2]},$$

due to light from LEDs L1 and L2 can be used to determine one or a plurality of properties of the biological fluid.

One envisioned embodiment of this invention is the use of two LEDs that can emit light at the same infrared wavelength to measure the red blood cells concentration (hematocrit) and flow rate of blood in the vessel, by calculating the ratio of optical reflectance measured using LEDs L1 and L2. Using the analytical model, this ratio, $$R = \frac{I_{det}[L1]}{I_{det}[L2]},$$

can be calculated and its sensitivity to hematocrit can be determined (see Graph below). The effect of hematocrit hct and blood oxygenation SpO2 can be incorporated into the analytical model by defining the absorption ($\mu_a^b$) coefficient, and hence the diffusion coefficient $k_b$, of the fluid as a function of hct and SpO2[3]:

[3] J. M. Schmitt, "Simple Photon Diffusion Analysis of the Effects of Multiple Scattering on Pulse Oximetry," IEEE Transactions on Biomedical Engineering, vol. 38, no. 12, December 1991.

$$k_b = \frac{1}{3(\mu_{a}^b[hct, SpO2] + \mu_s^b)}$$

Figure 9:
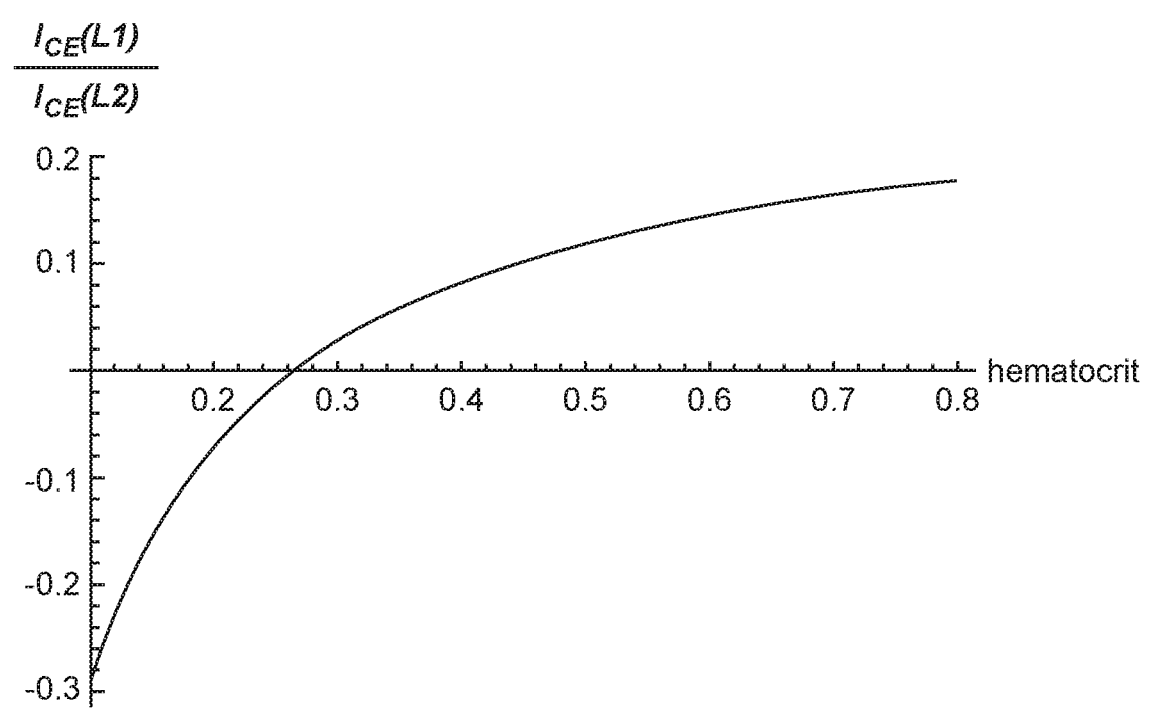
FIG. 9 is a graph of ratio reflected intensity at each spacing as a function of hematocrit.

FIG. 9 includes example plots of ratio, a $$R = \frac{I_{det}[L1]}{I_{det}[L2]},$$

as a function of hematocrit with an LED-PD spacing of $r_1$—5.3 mm and $r_2$—6.5 mm for L1 and L2, which indicates the ratio's sensitivity to increasing hematocrit. It should be noted, the negative values correspond to LED currents $I_{LED}$ below the minimum, threshold optical light intensity or LED current $I_{LEDth}$ needed to reach the vessel.

Further, blood volume flow rate Q can be estimated from the changes in the measured hematocrit hct using the ratio R over a cycle of pulsatile blood flow (i.e. one heart beat) in the vessel manifesting as a radial vessel dilation ΔD about its axis[4]. The blood volume under interrogation $Vol_{inter}$ in the vessel can be ascertained using the analytical model, by calculating the intersection of the LEDs' hemispherical irradiation volume and vessel at the operating point, i.e. optimal LED current $I_{LEDopt}$ for each of the at least two LEDs L1, L2. The blood volume flow rate measurement can be averaged over multiple cycles in order to increase measurement performance.

[4] R. R. Steuer et al., "Noninvasive transcutaneous determination of access blood flow rate," Kidney International, vol. 60, pp. 284-291, 2001.

$$Q = \frac{Vol_{inter}}{\oint \frac{1}{R}\frac{dR}{dt}dt}$$

Figure 10:
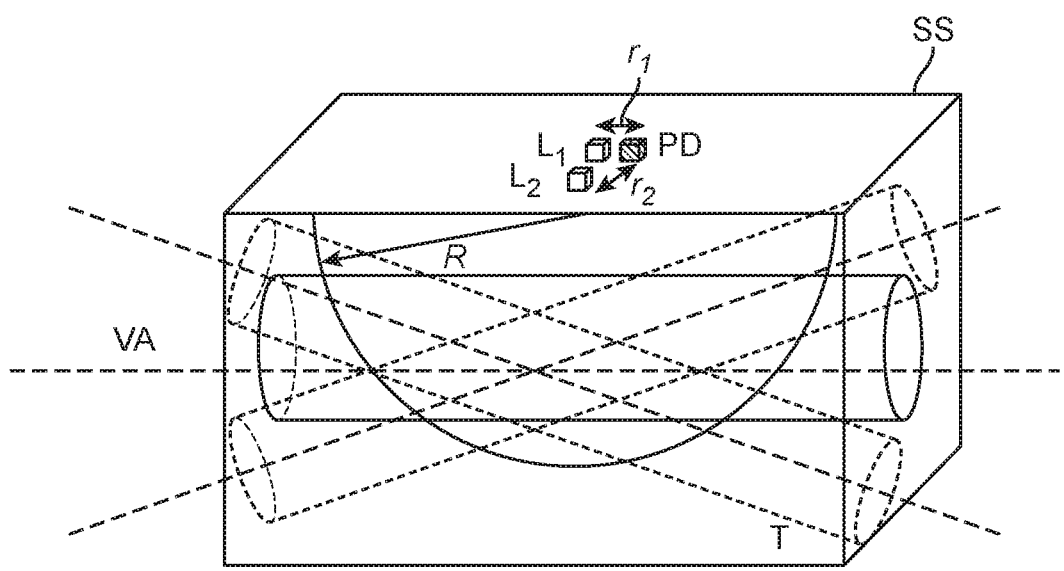
FIG. 10 is a schematic diagram of the system in FIGS. 2A and 2B illustrating a variation in vessel axis with respect to the hemispherical radiation volume induced by the LEDs.

The calculated interrogation volume $Vol_{inter}$ can be further adjusted to account for the variation in orientation of the vessel axis portrayed in FIG. 10. FIG. 10 is a schematic diagram of the system in FIGS. 2A and 2B illustrating a variation in vessel axis with respect to the hemispherical radiation volume induced by the LEDs. The system can account for this variation by using imaging sensors to detect the vessel axis position and refine the calculated interrogation volume $Vol_{inter}$. Alternatively, a correction factor C can be used to refine the interrogation volume $Vol_{inter}$ calculated using the analytical model, wherein C[d,D] can be defined as a function of the vessel depth d and diameter D by calculating the distribution of the volume intersection of the hemispherical optical radiation and a cylinder[5].

[5] W. Gille, "Chord Length Distributions of the Hemisphere," Journal of Mathematics and Statistics, vol. 1, no. 1, pp. 24-28, 2005.

Once the hematocrit, vessel dimensions, and volumetric flow rate have been determined, a number of clinical conditions can be monitored using the methods and embodiments described herein in conjunction with an appropriate remote monitoring system. When utilized as part of a remote monitoring system, the capabilities described herein can allow clinicians to better monitor a number of conditions, including but not limited to:

Arteriovenous (AV) Access Maturation

After an AV access is surgically created, there is often a maturation period that needs to occur for the body to adapt to the presence of new vessel. In the cases of a native AV access (referred to as a fistula), this maturation period can take up to 12 weeks. During this time, the patient is at high risk for access closure. If the access becomes closed, or fails to mature, the patient must then endure an additional surgery and subsequent maturation period, which can further delay the start of their dialysis treatments. Ultimately, this creates more risk for the patient, added cost to the healthcare system and complicates management of these patients for clinicians.

The most common cause of the access failing to mature is the development of a juxta-anastomotic stenosis, which reduces flow into the newly formed access. This condition is easily correctable if detected early enough, and when corrected leads to successful access maturation in most patients.

Monitoring the volumetric flow rate through a patient's AV access is a well-established way of assessing access maturation. A "mature" AV access is defined as one that can sustain 600 mL/min of flow.

Tracking the volumetric flow rate in an AV access during the maturation period is something that is impractical through in-clinic measurements, but could be addressed through a remote, at-home monitoring system. Incorporation of the methods and embodiments disclosed herein into a remote monitoring system would enable tracking of the maturation process of a patient's AV access. In such a system, the clinician could be alerted if the access needed intervention (e.g. to correct a juxta-anastomotic stenosis) or if the patient's AV access had matured and was ready to begin dialysis.

AV Access Health

After an AV access has matured and the patient has begun dialysis, the only reliable methodology for detecting a blockage within a patient's AV access remains a physical examination carried out by a trained nephrologist. This examination is recommended to be carried out once a week—something which is impractical given the volume of patients seen by a dialysis clinic.

A remote monitoring solution that automatically tracks the health of an AV access and can detect blockages in said access would enable better outcomes and compliance with clinically recommended best-practices.

Tracking volumetric flow rate is a clinically accepted approach for determining the health of a patient's AV access, and for determining whether the patient needs an intervention to preserve the health of the access. Incorporation of the methods and embodiments disclosed herein into a remote monitoring system would enable tracking of the health of a patient's AV access. In such a system, the clinician could be alerted if the access needed intervention (e.g. to correct a blockage). This would enable practical, and reliable monitoring of access health—leading to better outcomes and lower costs.

Dialysis Patient Dry Weight/Fluid Status

When a patient is on dialysis estimation of their "dry weight" is essential to understanding both end-dialysis weight targets and the necessary rate of dialysis to appropriately manage a patient's fluid level. No reliable metrics exist today to track this important parameter, and this value is determined predominantly through clinical judgment.

It is generally accepted that hematocrit levels are inversely proportional to patient blood volume, so long as a patient is not hemorrhaging or undergoing any other significant trauma that could lead to blood loss. The monitoring of hematocrit level can be more reliably used to make a determination on a patient's fluid status, if measured in conjunction with additional vitals such as heart rate, blood pressure, and flow.

The embodiments and methods disclosed herein could be incorporated with a remote monitoring system to track fluid status of a patient on dialysis and to develop a quantified assessment of dry weight over the course of multiple dialysis sessions. This technology could be applied to vessels close to the surface of the skin such as an AV access, radial artery, brachial artery, carotid artery, etc. The flexibility of this approach could allow for fluid status monitoring for patients on peritoneal dialysis as well as for those on hemodialysis.

Fluid Overload or Dehydration in Congestive Heart Failure Patients

Congestive heart failure (CHF) patients often must undergo hospitalization for fluid overload or dehydration, which has a significant effect on increasing the mortality rates for these patients. The goal for CHF patient management is to provide fluid management that enables the patient to stay in fluid balance, without becoming dehydrated or overloaded.

Hematocrit, blood pressure, oxygen saturation, and blood flow rate are all useful metrics in diagnosing a patient's fluid status. The methods and embodiments described herein could be used in conjunction with a remote monitoring system to detect and monitor fluid status of patients and thus enable fluid management of patients with congestive heart failure. An exemplary embodiment of such a system would determine a patient's fluid level through measurement of hematocrit, heart rate, blood pressure and oxygen saturation. After determining the patient's fluid level, the system would provide a recommendation on the patient's intake of fluid and sodium for that day, while also notifying the clinician that such a recommendation had been made. In this embodiment, if a patient were at risk of becoming overloaded or dehydrated, the system would alert the clinician so that additional recommendations and tests could be carried out.

The embodiments and methods described herein could be utilized in a wearable device that is used as part of a remote monitoring system to provide non-invasive fluid management for heart failure patients. The wearable device could be worn over a suitable blood vessel close enough to the surface of the skin, such as an AV access, radial artery, brachial artery, carotid artery, cephalic vein, etc.

Fluid Status for Patients in Critical Care Units

Patients in critical care units who are hypotensive are candidates for fluid bolus therapy to preserve blood pressure and cardiac function. However, in 50% of cases, patients are operating at peak cardiac output, and providing additional fluids will exacerbate any cardiac issues rather than solving the observed hypotension.

The most reliable method of determining a patient's suitability for fluid bolus is to perform a fluid challenge and test the cardiovascular fluid response. Cardiovascular fluid response has traditionally been monitored using a pulmonary artery catheter (PAC). This requires a surgical procedure to be carried out on an already critical patient. Another approach is to monitor bioimpedance noninvasively using electrodes on the patient's chest and torso. This approach doesn't require a surgical procedure, but is still a complicated process since multiple electrodes have to be applied in the correct locations to get a measurement. Moreover, this system is very costly for critical care units and is difficult to uniformly use across all patients.

A wearable, low-cost solution for monitoring fluid status in critical care patients would offer a significant advantage over current approaches for fluid status monitoring.

The methods and embodiments described herein could be incorporated into a remote monitoring system that comprises a wearable sensor to provide monitoring and measurement of patient fluid status. The measurement of hematocrit, in conjunction with other metrics (heart rate, blood pressure, oxygen saturation and flow rate) could provide an accurate estimate of fluid status without the need for a surgical procedure, or costly equipment. The wearable sensor could be applied over any suitable vessel lose enough to the surface of the skin, such as an AV access, radial artery, brachial artery, carotid artery, cephalic vein, etc.

4. Example Method for Measuring Fluid Vessel Properties

Figure 11:
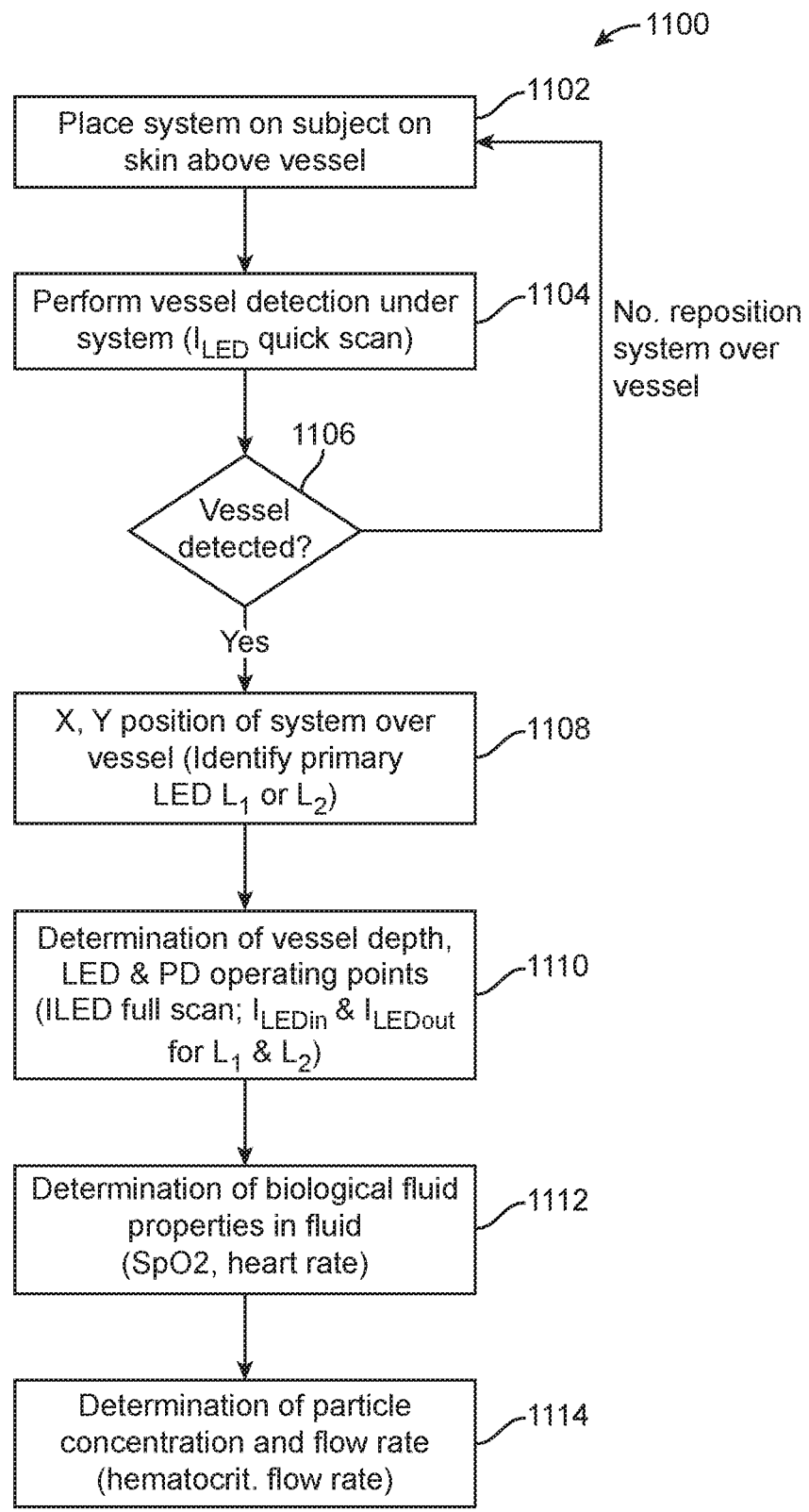
FIG. 11 is a flowchart illustrating operation of a system for measuring one or a plurality of biological fluid properties using an example of the system in FIGS. 2A and 2B positioned on the skin surface of a patient.

In an example implementation, the system may operate as illustrated in the flowchart 1100 in FIG. 11. At step 1102, the system may be placed on the surface of a patient's skin at a position above a fluid vessel disposed in the tissue below the skin. The LEDs are energized at step 1104 for a quick scan of the tissue. The LEDs emit light at different intensities and reflectance signals are received at the photodetector for each intensity. The reflectance values are analyzed to determine if the fluid vessel has been detected (decision block 1106). If the fluid vessel is not detected ("NO" path from decision block 1106), the system may be re-positioned on the skin surface and the method begins again at step 1102. The reflectance values may provide the user with some indication as to which direction and the user may use the reflectance values to guess as to a distance and direction from the current position of the system. If the vessel is detected ("YES" path from decision block 1106), the position of the system relative to the fluid vessel may be determined at step 1108. The system may be in an off-axis position relative to the vessel, and likely not centered over the vessel. The system may illuminate each light source with different levels of intensities to measure reflectance values allowing the system to determine which light source is a primary light source (I.e, the light source having an illumination volume that covers more of the vessel than the other light source). The light source and the photodetector can be moved in a direction transverse to the blood vessels such that the light sources cover a more equal part of the vessel. This process of repositioning the light sources and photodetector may be repeated until the light sources and photodetector are substantially centered over the vessel. Steps 1102 through 1108 may then be repeated.

At step 1110, the system at a known position relative to the fluid vessel may be used to determine a depth of the fluid vessel and the diameter of the vessel. The system may also determine certain operating parameters used in determining the properties of the vessel, such as for example, a threshold LED current, $I_{LEDth}$, an optimum LED current, $I_{LEDopt}$, for each LED. The threshold LED current for each LED is the minimum current level needed to irradiate the region below the LEDs and for their respective optical radiation radii to reach the vessel. The optimum LED current is a current level needed to irradiate the region below LEDs and for their respective optical radiation radii to reach beyond the bottom of the vessel. Also, at step 1110, the LEDs and the photodetector may perform scans the tissue beneath the LEDs at different intensities and in some cases at different wavelengths to obtain reflectance values at each intensity.

At steps 1112 and 1114, the reflectance values received from performing the scan in step 1110 may be analyzed to determine certain properties or obtain measurements of the fluid vessel. The properties comprise blood oxygenation (SpO2), heart rate, hematocrit, hemoglobin concentration, analyte concentration, chemical composition, particle flow rate, blood flow rate, and/or other properties.

Figure 12A:
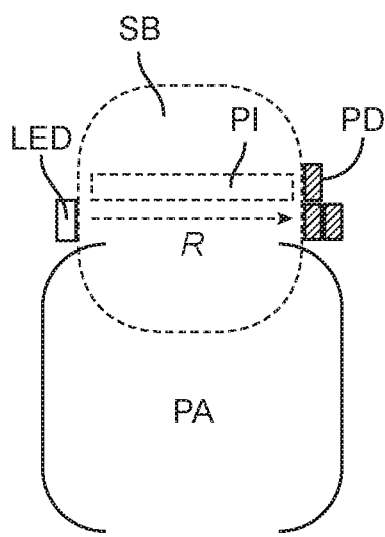
FIGS. 12A and 12B are front views at extension and at flexion of a knee of a patient with a system for measuring one or a plurality of biological fluid properties thereupon.
Figure 12B:
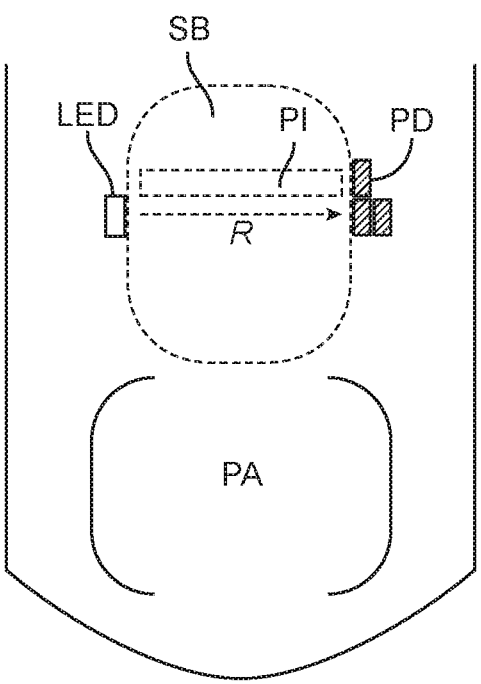

In another example implementation, the system may operate as illustrated in the flowchart 1300 in FIG. 13A. At step 1320, the system may be placed on the surface of a patient's skin at a position superior to the patella PA as shown in FIGS. 12A and 12B. The LEDs are energized at step 1340 for a quick scan of the tissue. The LEDs emit light at different intensities and reflectance signals are received at the photodetector PD for each intensity. The reflectance values are analyzed to determine the depth of the bursa SB containing synovial fluid (step 1340). Once the depth of the bursa has been determined, the device will read z-values from the onboard accelerometer and the resistance signal from the piezoelectric film PI to determine the knee's angle of flexion (decision block 1360). If the angle of flexion is greater than 45°, the device will read data from all onboard sensors, including but not limited to the photodetector array 1304A-B, MEMS microphone 1309, temperature 1307 and accelerometer. If, at the time of interrogation of the accelerometer and piezo 1305, the angle of knee flexion is less than 45°, the device will wait 15 seconds before interrogating the angle of flexion again. The device may also provide haptic feedback to alert the patient to the need to flex their knee. This data is transmitted via a wireless communications protocol such as Bluetooth® Low Energy (BLE) to a remote hub unit. The hub unit relays the received data to a cloud serve via a 3G cellular network. In the cloud server, the data is analyzed to diagnose a variety of disease states, including but not limited to periprosthetic joint infection, loosening of the orthopedic implant, fracture of the orthopedic implant, and fracture of the bone surrounding the orthopedic implant. This diagnosis is made using a composite of multiple measurements taken over the course of multiple days.

It is noted that the example method in FIG. 11 is only one example of the use of the systems described herein. Other methods may be used as well.

It is noted that the example system in FIGS. 1 and 13B are examples of systems incorporating a system for measuring biological fluid properties. The optical detection techniques described herein may be incorporated into a wearable monitoring system described below, such as for example, the system of FIGS. 15 and 16. Additionally or alternatively, an optical sensor of the present disclosure may comprise an example, variation, or embodiment of optical systems for measuring biological fluid properties described herein.

II. Wearable Monitoring System

1. System Overview

Disclosed herein are systems and methods for monitoring a patient. In an example implementation, a system for monitoring a patient comprises a wearable device, or a wearable patch, configured to attach to a body part of a patient. The wearable patch includes a sensor assembly mounted on the wearable patch. The sensor assembly comprises a plurality of sensors configured to detect a corresponding plurality of sensory modalities and generate one or a plurality of electrical signals representing the sensory modalities. The wearable patch comprises a signal converter configured to receive the one or a plurality of electrical signals from the plurality of sensors and to convert the signals to one or a plurality of sensor data signals comprising a data representation of at least one of the one or a plurality of electrical signals. A communications interface communicates the one or a plurality of sensor data signals to a sensor data processing system. The wearable patch is attached to a patient to take measurements based on the sensors included in the sensor assembly. The data from the sensors is communicated to the sensor data processing system.

As used herein, the terms "close proximity," "local," "locally," "substantially close," or "near" in reference to a patient wearing a wearable device or patch shall mean within a distance at which the communication interface on the wearable patch communicates using Bluetooth® Near-Field Communication (NFC), near field magnetic communication, a wired connection, or any wireless technology configured for communication with a building. Communications over distances typically by cellular, WiFi™ to the Internet, the Internet, satellite, or any other technology configured for communication beyond a building shall be understood to be "remote," "far," or at a "long distance."

In an example implementation, the communication interface on the wearable patch transmits one or a plurality of sensor data signals, processed measurements, or alerts indicating that more thorough examination of the patient may be required, to a local hub using a first protocol configured for local or near distance communications. The local hub communicates the one or a plurality of sensor data signals to a remote sensor data processor over a second protocol configured for long distance communication. The first protocol may comprise Bluetooth®, near field communication protocols, near field magnetic protocols, or any communication protocol configured to provide communications over a short distance. The second protocol may comprise cellular communications, WiFi™ communication via the Internet, satellite communications, and other long distance communications protocols. In the second protocol, a local hub is not required. In one example, a local hub may be implemented as an application on a smartphone using Bluetooth® to receive one or a plurality of sensor data signals from the wearable patch. The wearable patch and the smartphone may process the one or a plurality of sensor data signals to a desired extent, or may simply relay the one or a plurality of sensor data signals to the remote sensor data processor using a WiFi™ connection to the Internet or a cellular data connection.

The sensor data processing system, which may comprise the local hub and the remote sensor data processor may comprise an interface to a patient medical records database, any suitable database, or a web portal. The sensor data processing system may also comprise an alerting system to send notifications of conditions requiring urgent attention to a doctor or any other specified person. The notifications may be sent using any suitable communications system such as, for example, notification via e-mail, notification on a website, notification by text message, or any other suitable signaling mechanism.

The sensor assembly on the wearable patch may comprise any combination of sensors. For example, sensors included in example implementations of the sensor assembly may comprise any combination of the following:
 1. acoustic sensors
 2. accelerometers
 3. strain gauges
 4. temperature sensors
 5. pressure sensors
 6. optical sensors
 7. moisture sensors
 8. conductivity sensors
 9. chemical sensors In some implementations, an ultrasonic transducer may be disposed in the sensor assembly along with ultrasonic sensors to obtain ultrasonic imaging of a desired body part.

In some implementations, the sensor assembly may be configured for specific applications by selecting sensors that provide information that may be used to determine a state of a certain condition. In one example, the wearable patch may be configured to monitor an arteriovenous (AV) fistula on a dialysis patient. The wearable patch may comprise a sensor assembly having an acoustic sensor, an accelerometer, a strain gauge, and two thermometers. The acoustic sensor may be a microphone designed to have a flat sensitivity between 20 Hz and 20 kHz. The accelerometer may be selected to be sensitive along three axes from DC to 500 Hz. The strain gauge may be selected to have a sensitivity to mechanical strain between 0.1 Hz to 20 MHz. The temperature sensors may be selected to have resolutions below 0.1° C. and sample up to 8 Hz.

Figure 14:
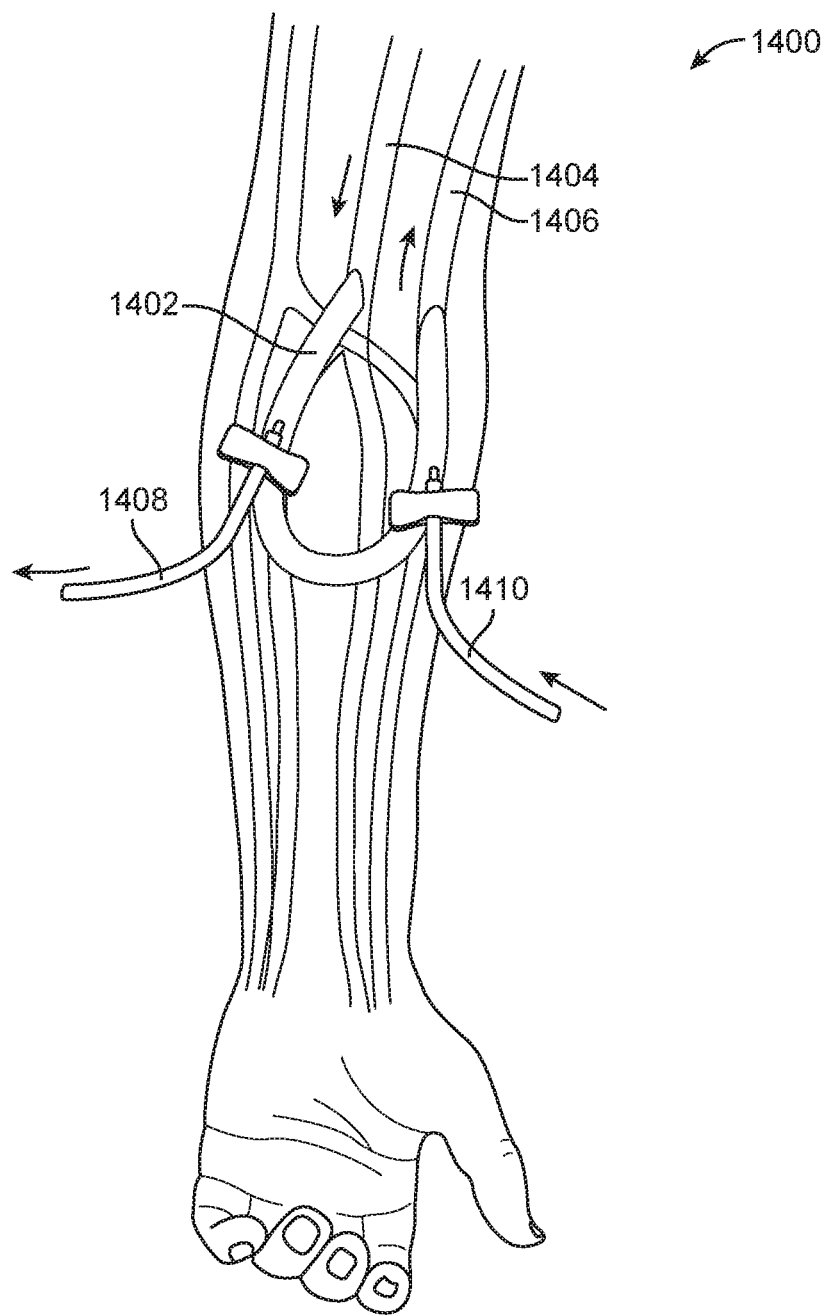
FIG. 14 depicts an arm having a synthetic bridge graft between an artery and a vein.

In the example application, the wearable patch may be applied to the surface of a patient's arm over an AV fistula, which may be used for kidney dialysis. Dialysis patients may have a fistula (natural vein) or synthetic graft inserted to provide access to blood flow for dialysis treatments. FIG. 14 depicts an arm having a synthetic bridge graft used as an AV fistula between an artery and a vein. Referring to FIG. 14, an arm 1400 having an arteriovenous (AV) access 1402 inserted to receive blood from an artery 1404 and to transport the blood to a vein 1406. A first catheter 1408 is inserted into the AV access 1402 on the arterial side to transport blood to a dialysis machine (not shown). A second catheter 1410 is inserted on a venous side to transport blood from the dialysis machine back into the vein 1406.

The AV access 1402 may become occluded over time during use and prevent the patient from receiving dialysis treatment. The blockage can typically either be acute from thrombosis or occur over time through stenosis. If blockage is detected early enough, there are treatments that can unclog the AV access (e.g. thrombectomy, angioplasty) while preserving the access. If a thrombosis forms, clinicians must intervene prior to the thrombus hardening (typically occurs within 48-72 hours) order to successfully treat the patient and preserve the access. If left untreated, the access may need to be replaced which leads to 4-12 weeks of catheter-based dialysis in the patient's treatment. Central catheters carry several risk factors for patients (e.g. infection, easily blocked, etc.) and as a result, their long-term inclusion in a patient's dialysis protocol is considered to be an indicator of poor quality of care for the dialysis patient by organizations such as the Center for Medicare Services (CMS) and the National Kidney Foundation.

The output of the microphone provides an acoustic signature of the flow within the fistula. The accelerometer provides several pieces of information. For example, the accelerometer generates data indicative of the orientation of the arm with respect to gravity from the DC component of all three axes. The accelerometer may also be used to determine if the arm is in motion during the reading of the data, which in turn may be used to determine if the motion of the arm was sufficient to affect the readings from the other sensors. The accelerometer may also provide a ballistic cardiographic measurement in the location of the fistula. The strain gauge provides information about the strength of the pressure wave through the fistula as it forces expansion on the surface of the skin. The two temperature sensors provide a differential measurement of skin temperature in the region of the fistula relative to a location without significant arterial flow. Thermography is as a tool for determining the state of healthy blood flow in the periphery.

The sensor assembly fitted with the above-described sensors provides multiple and simultaneously collected data streams at any given time. The combination of these simultaneous data streams provides a more complete and accurate assessment of the quality of blood flow within the fistula, more than any single data stream can provide individually. The specific signature of the multiple data streams processed together can provide diagnostic information to the clinician as to the source of any change in the condition of the fistula.

Figure 15:
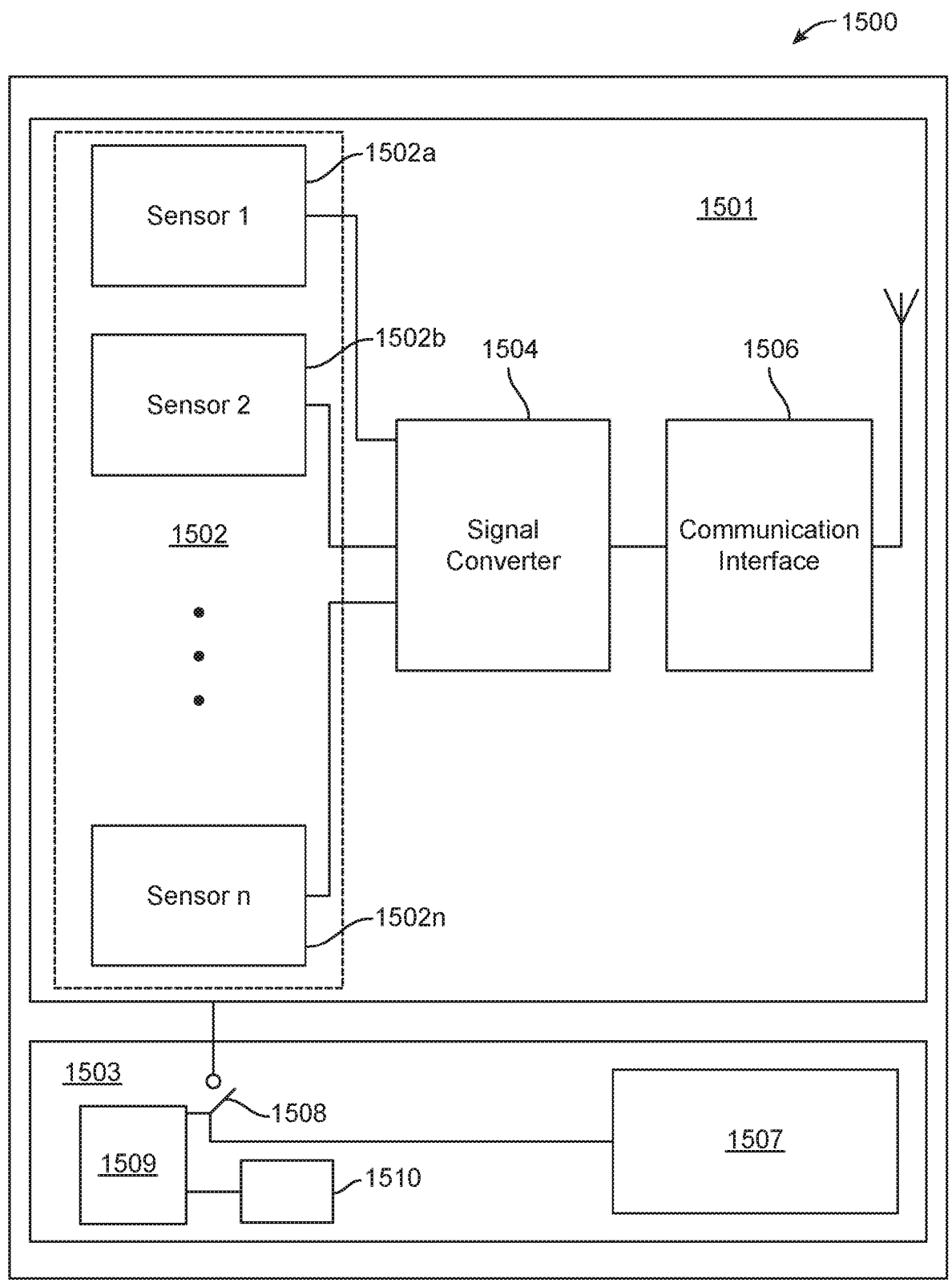
FIG. 15 is a block diagram of an example implementation of a wearable patch with a sensor assembly and a wireless communication interface.

FIG. 15 is a block diagram of an example implementation of a wearable patch 1500 comprising a sensor control module 1501 and a power module 1503. It is noted that the block diagram in FIG. 15 is schematic such that components are described in functional hocks for clarity with no intent to limit the described examples to any number of modules. An example implementation may comprise separate hardware modules implementing the sensor control module 1501 and the power module 1503. In other implementations, a single hardware module, e.g. a circuit board, may comprise components of both the sensor control module 1501 and the power module 1503.

The sensor control module 1501 comprises a sensor assembly 1502 and a wireless communication interface 1506. The sensor assembly 1502 comprises N sensors, sensor 1502a, sensor 1502b, and additional sensors up to sensor 1502n. Each sensor 1502a-n detects a corresponding sensory modality and converts the sensory modality to an electrical signal. The electrical signal is communicated to a signal converter to convert the electrical signal to a suitable data representation of the one or a plurality of properties indicated by the electrical signal. For example, the acoustic sensor may be a microphone or a piezoelectric transducer. Sound is converted to one or a plurality of electrical signals in a well-known manner producing a signal having a frequency and an amplitude. The electrical signal may be processed by amplifying the signal and filtering the signal to reduce any noise that may be in the signal. The electrical signal may then be input to a signal converter 1504 to convert the electrical signal to data. The signal converter 1504 may comprise an analog-to-digital converter (ADC) to generate a series of digital samples representing a voltage level at each part of a wave formed by the electrical signal. The signal converter 1504 may also comprise a processor to perform, for example, digital signal processing techniques to either reduce the data set to comprise only the most meaningful data, to filter out signal anomalies, or to perform other similar functions. The processor may also comprise functions to manage the operation of the wearable patch 1500. For example, the processor may be programmed to implement an operating system, such as for example, a state machine in which the components are controlled according to various states. Other types of operating systems may also be used, such as an infinite loop of control functions for acquiring sensor data, and managing the power during times in which the wearable patch is not acquiring sensor data. The processor may operate using interrupt schemes, or polling of input/output (I/O) devices to control the functions of the wearable patch 1500. The processor may be programmed to perform minimal processing of the data, or to perform signal conditioning functions or to perform more high level functions such as analysis sufficient to determine if an alert should be communicated. In some implementations, the digital signal processing and other high level functions may be performed by the sensor data processing system, which may be at the local hub in a system that comprises the local hub.

Each sensor 1502 may be connected to provide one or a plurality of electrical signals to the signal converter 1504 to form channels of sensor data. The signal converter 1504 may be configured to provide signal processing functions tailored to the sensor 1502 connected to the signal converter 1504. The signal converter 1504 may also comprise functions to format the simultaneously collected data as a sensor data signal in a manner that permits the sensor data signal to be communicated. The signal converter 1504 communicates the sensor data signal to the communication interface 1506 for transmission to the sensor data processing system. In some implementations, the sensor data may be combined into a single sensor data signal. In other implementations, the sensor data may be formatted in one or a plurality of sensor data signals that correspond to each sensor from which the data is obtained. That is, the sensor data signal may be communicated as a single data stream that combines the sensor data from each sensor, or as multiple data streams each having the sensor data from a corresponding sensor.

The communication interface 1506 may be configured to operate using any suitable communications protocol. A wireless communication protocol is preferred, although a wired communication protocol may be used as well. In an example implementation in which the wearable patch 1500 communicates with a local hub, which then communicates with a remote sensor data processor, the communication interface 1506 may comprise functions enabling communication using communication protocols for short distance communication. The communications interface 1506 may also communicate using communication protocols for short distance communication to transmit one or a plurality of sensor data signals to a locally placed sensor data processing system. The system data processing system may provide monitoring functions, diagnostic functions, and may interface with locally or remotely located databases or web portals. The system data processing system may also comprise functions to send alerts by email, text messages, or other available formats.

The power module 1503 comprises an energy source 1507 such as, for example, a battery or other portable energy source that may be of limited capacity. The power module 1503 may be configured to operate in a low power state. In an example implementation, the power module 1503 may be configured to operate in a state in which the components on the sensor control module 1501 are isolated from the energy source 1507 be a power switch 1508 as shown in FIG. 15. The low power state, or the state in which power is switched off permit the wearable patch to implement functions that conserve energy.

In an example implementation, the power module 1503 may comprise a wakeup sensor 1509 to change the state of the power switch 1508 to provide power to the sensor control module 1501 to begin operate, such as acquisition of sensor data. The wakeup sensor 1509 may be implemented using a watchdog timer that times up, or down, to, or from a time period. When the time period elapses, the watchdog timer may switch the power switch 1508 to power the sensor control module 1501 and to signal the processor to perform needed functions, such as acquisition of sensor data, or other processing functions. In example implementations, the wakeup sensor 1509 may comprise a sensor that detects activity at one or more of the sensors 1502a-1502n. For example, the wakeup sensor 1509 may comprise a signal detecting function in which an electrical signal from one or more sensors of sufficient magnitude to constitute a meaningful signal from the sensors is detected as a trigger to power the signal control module 1501 to begin acquisition.

In some implementations, the wakeup sensor 1509 may be a sensor of selected states that indicate conditions for which power should be provided to the signal control module 1501. For example, the wakeup sensor 1509 may comprise any combination of the following:

1. Magnetic sensors or switches
2. Optical sensors
3. Motion, acceleration or tilt sensors
4. Temperature sensors
5. Capacitive proximity sensors
6. Mechanical switches The wearable patch 1500 may also comprise functions and components to support long term storage of the wearable patch 1500. For example, the wearable patch 1500 may operate in a "shelf mode." The shelf mode may be entered via explicit control (e.g. a command) received from a device communicating over the communication interface 1506. In some implementations, the shelf mode may be entered based on one of the sensors 1502a-n (which may comprise the wakeup sensor 1509). In some implementations, the shelf mode may be entered based on a specific shelf sensor 1510 as shown in FIG. 15. When in shelf mode, the various components of the wearable patch 1500 may be commanded to enter a low power mode, or may be cut off from power by the power switch 208, or other switches selectively inserted to control selected sensors 1502. The shelf mode can be exited based on the wakeup sensor 1509, any one or more of the other sensors, 1502, or via the specific shelf sensor 1510, which may be configured to automatically detect the wearable patch 1500 being put into service. This shelf sensor 1510 may be implemented using any combination of the following:

1. Magnetic sensors or switches
2. Optical sensors
3. Motion, acceleration or tilt sensors
4. Temperature sensors
5. Capacitive proximity sensors
6. Mechanical switches This shelf sensor 1510 may interact with the packaging 1500 in which the wearable patch is stored prior to deployment on a patient. When the wearable patch 1500 is in its packaging, it is in shelf mode thereby precluding a connection of the power from the energy source 1507 to the sensor control module 1501. In some implementations, the packaging may be configured to generate a magnetic field which is detected by a shelf sensor 1510 capable of sensing magnetic fields to prevent the wearable patch 1500 from being activated and thereby consuming power. In an example implementation, the wearable patch 1500 may be provided with an adhesive liner during manufacturing. The adhesive liner is configured so that a user would remove the adhesive liner during application of the wearable patch 1500 on the patient. The adhesive liner may be made of a material that generates a magnetic field. When the magnetic adhesive liner is removed to apply the wearable patch 1500 on the patient, the magnetic field is removed as well so that the shelf sensor 1510 can no longer detect the magnetic field. When the magnetic field is not detected, the wearable patch 1500 is taken out of shelf mode and allows the energy source 1507 to power the sensor control module 1501.

In other implementations, the packaging may be opaque to light and the shelf sensor 1510 may be a light sensor. If the wearable patch 1500 is in its packaging, the shelf sensor 1510 does not detect light and keeps the wearable patch 1500 in the shelf mode precluding the energy source 1507 powering the sensor control module 1501. When the wearable patch 1500 is removed from the packaging, the shelf sensor 1510 is exposed to ambient light allowing the shelf sensor 1510 to sense the ambient light and determine that the wearable patch 1500 has been removed from its packaging. The shelf sensor 1510 changes to a state in which it is no longer in shelf mode to enable the delivery of power to the sensor control module 1501.

2. Example Implementation of a Wearable Patch.

Figure 16A:
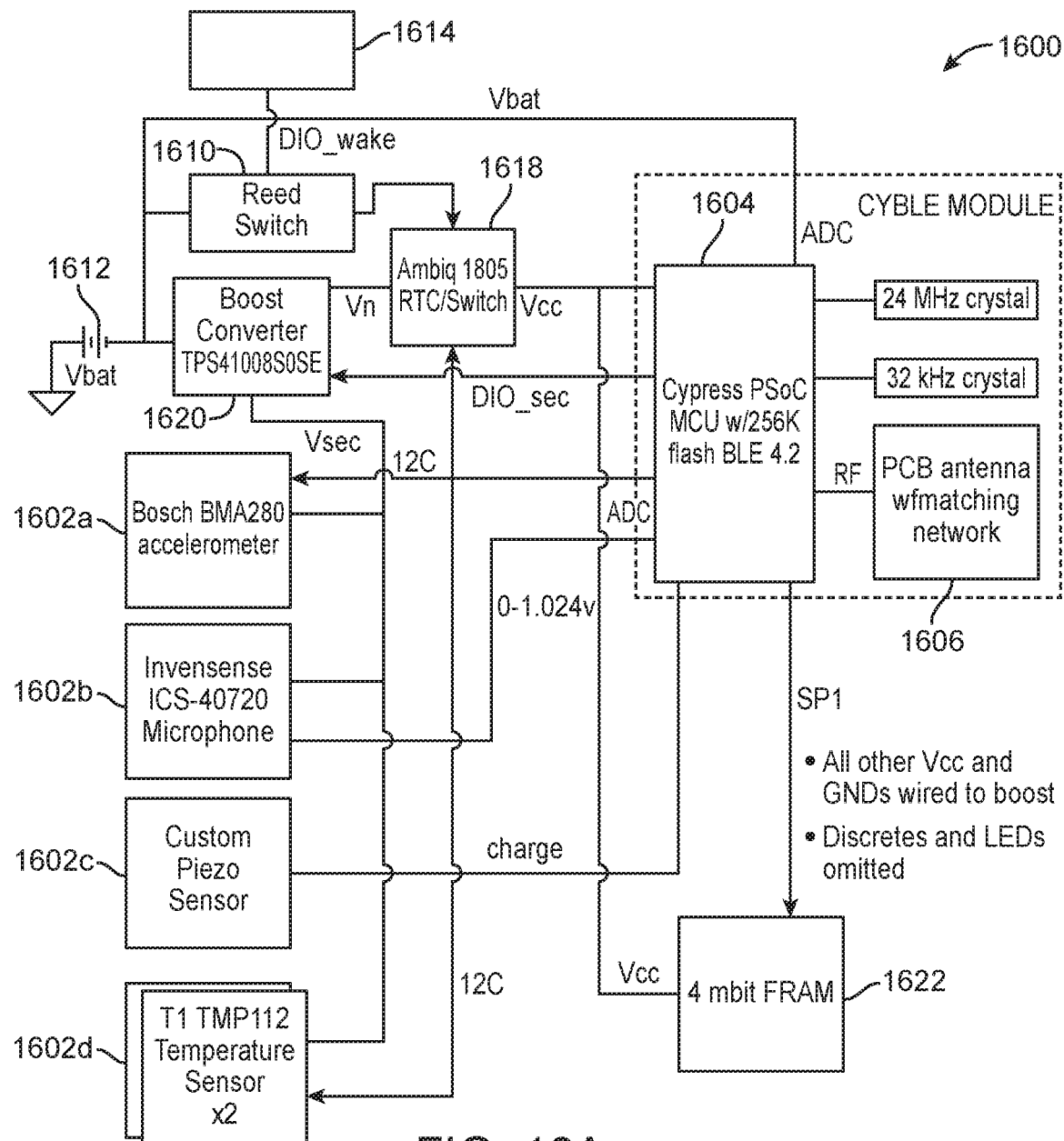
FIG. 16A is a block diagram of another example implementation of a wearable patch with a sensor assembly and a wireless communication interface.

FIG. 16A is a block diagram of another example implementation of a wearable patch 1600 with a sensor assembly 1602 and a wireless communication interface 1606. The wearable patch 1600 in FIG. 16A comprises a sensor assembly comprising an accelerometer 1602a, a microphone 1602b, a piezoelectric sensor 1602c, and two temperature sensors 1602d. The sensors 1602 indicate specific components that may be used as the sensors in the sensor assembly in FIG. 16A. The accelerometer 1602a may be implemented using a Bosch BMA280 accelerometer. The microphone 1602b may be implemented using a Knowles SPH1642 MEMS microphone. The strain gauge 1602c in FIG. 1602c is indicated as being a custom piezo sensor. The temperature sensors 1602d may be implemented using two TI TMP 112 temperature sensors. It is noted that the specific parts identified for implementing the sensors 1602 in the sensor assembly are only examples of components that may be used as each sensor. Many components are available for use as each sensor. Those of ordinary skill in the art will appreciate that suitable sensors may be selected based on the specific requirements of specific implementations.

It is noted that the example described below is for a wearable patch intended for operation by communicating to a local hub, which then communicates data to a remote sensor data processor.

The sensors 1602 in FIG. 16A are connected to communicate with a processor 1604, which comprises ADC functionality and other signal conditioning functions. The processor 1604 converts the one or a plurality of electrical signals from each sensor to one or a plurality of sensor data signals for communication via the communication interface 1606.

The wearable patch 1600 in FIG. 16A is one example implementation of a wearable device for simultaneously obtaining data from multiple sensory modalities detected using multiple sensors. The operation of the wearable patch 1600 in FIG. 16A is described as follows. Those of ordinary skill in the art understand the implementation details described below are provided as examples, and are also able to identify and use alternatives.

The wearable patch 1600 is configured to capture data from 4 or fewer analog channels plus devices connected by an inter-integrated circuit (I2C) bus. One channel is used to communicate one or a plurality of electrical signals representing sound from an analog MEMS microphone. An example of an analog MEMS microphone that may be used in the wearable patch 1600 in FIG. 16 is a SPH1642 MEMS microphone from Knowles. The remaining channels correspond to the Bosch BMA280 accelerometer, the two TI temperature sensors running over the I2C bus and 1 charge-amplified channel for piezo sensing.

3. Sensor Read Process.

Data may be sampled for a predetermined read duration time (such as for example, 5 seconds) on selected channels. The temperature sensors may be sampled once, at the beginning of the measurement. Analog microphone data may be sampled by an ADC, such as for example, the 12 bit SAR ADC function on the processor, at a selected sample rate (for example, 4 kHz) at a selected resolution (for example, 12 bits). Data from the accelerometer may be sampled at a selected accelerometer sampling rate (for example, 1 kHz), at a selected resolution, which may also be 12 bits of resolution. The accelerometer may also be set to an anti-aliasing cutoff frequency (for example, 500 Hz).

The microphone 1602b may be operated in differential mode. In the illustrated example, operating in a differential mode may allow for an amplitude of 0.79 VRMS maximum, achieved at 123 dBA SPL. If 2 channels or fewer are used, the analog front end may comprise a 2nd order Butterworth type II anti-aliasing filter with a −6 dB predetermined cutoff frequency (for example, 1.6 kHz). If 3-4 channels are needed at the same frequency, the sampling rate may be increased and a single pole anti-aliasing filter may be used with a −3 dB frequency of around 4 KHz in the illustrated example.

The gain of the front end for each analog channel may be independently programmable via a configuration block, for example, by selecting among resistors, for example, on several output ports. Gains of 1×, 5× and 20× may be pre-installed on switchable input pins. A digital filter may be implemented to block 60 Hz AC frequency noise from the microphone, piezo and accelerometer channels. Data may be captured into RAM in a 251 byte (each half) double buffer. Once a buffer is filled, data capture may continue in the second buffer, and data in the first buffer may be filtered, delta compressed, and stored in FRAM without interrupting data capture.

Data reads may comprise a UTC timestamp in 32 bit unsigned Unix time. Unsigned 32 bit is used to save bytes, since there will be no data from before Jan. 1, 1970. This is followed by a 16-bit millisecond offset from that time (in the first packet) and a sequence number thereafter.

4. Sensor Suite Selection.

Several classes or types of sensors may be used in the sensor assembly and selected based on their ability to transduce clinically relevant data. Sensor suites may be configured in which the sensors are selected for their relevance to specific applications. The wearable patch 1600 in FIG. 16A comprises one or more of the following sensors to perform the indicated functions:

1. Microphone—a microphone may be incorporated into the wearable patch to measure the acoustic signature of blood flow through the fistula. This is consistent with current clinical practices and most closely resembles the use of a stethoscope to assess the health of an AV fistula.
   a. The microphone may be a MEMS microphone that is held directly against the skin by the surrounding adhesive of the wearable device. The MEMS microphone may also be protected by a thin-film porous membrane such as made from polytetrafluoroethylene (PTFE) that allows good acoustic coupling to the skin while protecting the MEMS microphone from moisture and particles.
   b. The microphone may be made of a piezoelectric material, such as for example, polyvinylidene fluoride (PVDF) or lead zirconate titanate (PZT). PVDF has an acoustic impedance very similar to biological tissue. A PVDF sensor that is conformally attached to the skin can offer unique benefits to stethoscope design by allowing for elimination of impedance matching components that add to the bulk of traditional stethoscopes. The PVDF sensor may be attached directly on the skin in the area of the fistula using a biocompatible adhesive with suitable acoustic impedance. An exemplary adhesive would be a hydrogel adhesive, which typically has comparable acoustic impedance to biological tissue and PVDF.

2. Accelerometer—the accelerometer allows for:

Detection of fistula health by monitoring the vibration or thrill that can be detected from the flow of a healthy fistula Detection of arm motion that would interfere with a good read.

Use as in inclinometer to monitor the orientation of the arm relative to gravity.

3. Temperature sensor:

Pair of temperature sensors at different locations on the user's arm differentially may be used to infer blood flow in the fistula.

4. Piezoelectric sensor (strain gauge) may take the form of a stretched piezoelectric diaphragm or a piezoelectric sensor in compression driven by a diaphragm and will produce an AC acoustic signal.

5. Power Management/Shelf Mode.

The wearable patch 1600 comprises a shelf mode wakeup sensor 1610, which may be implemented as shown in FIG. 16 using a, normally closed magnetic reed switch connected to a battery 1612. The shelf mode wakeup sensor 1610 cuts off power from the battery 1612 to the rest of the system when the shelf anode wakeup sensor 1610 is open. The wearable patch 1600 may be stored prior to deployment in packaging that comprises a magnetic adhesive backing liner 1614 applied to adhesive on the wearable patch 1600. When the magnetic adhesive backing liner 1614 is attached to the wearable patch 1600, the shelf mode wakeup switch 1610 is kept in an open state by the magnetic field from the adhesive backing liner 1614 thereby keeping battery power disconnected from the other components. When the adhesive backing liner 1614 is removed during deployment of the wearable patch 1600 on the patient's body, the shelf mode wakeup switch 1614 closes, thereby restoring power to the remaining components on the wearable patch 1600. Once power is present, the wearable patch microcontroller 1604 actuates a shelf mode lockout switch 1616, which prevents the shelf mode wakeup switch 1614 from returning the device to shelf mode without an explicit command from the microcontroller 1604 to unlock the shelf mode lockout switch 1616.

Figure 16B:
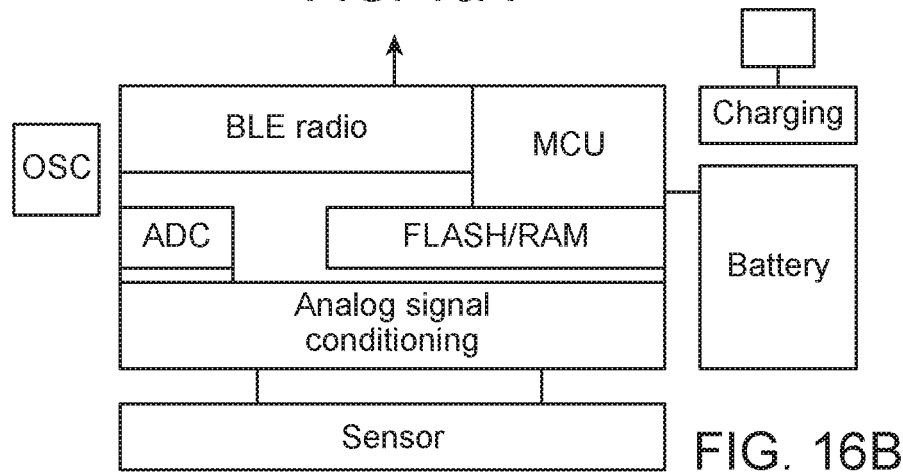
FIG. 16B is a flow diagram for an example state machine for the wearable patch of FIG. 16A.

The wearable patch 1600 in FIG. 16B comprises a power switch 1620, which may be implemented using a nanoboost converter with integrated load switch. In the illustrated example, the power switch 1620 applies battery voltage to two 3.0 V. buses: 1. Vcc, which is used to power the processor 1604, and 2. Vsec, which is used to power the sensors and a memory module 1622. The power switch 1620 consumes power at nA levels in a quiescent (low power/low demand) state.

The wearable patch 1600 also comprises a wakeup sensor 1618, which may be implemented using an Ambiq 1805 nanopower RTC+switch. The wakeup sensor 1618 maintains a timestamp and powers up the processor 1604 on a time schedule. The processor 1604 provides power to a secondary bus as needed by wearable patch 1600 application via a digital I/O output from the processor 1604 configured to drive the power switch 1620. Before entering a sleep mode, the processor 304 deactivates the secondary bus.

Between data reads and transmits, the processor 1604 may enter a deep sleep mode with the watchdog timer (wakeup sensor 1618) set to wake it on schedule. The boost converter load switch (power switch 1620) may be used to shut off all power to the memory 1622, the accelerometer 1602*a* and the microphone 1602*b*.

6. Firmware Flow.

A. Modes of Operation. Operation of the wearable patch 1600 may be implemented using a state machine according to a state diagram, such as the state diagram depicted in FIG. 16B. The state diagram in FIG. 16B operates using 8 basic states of operation as follows:

1. Shelf—the device has been put on the shelf for long-term storage. Power is disconnected from the system and can only be reconnected by actuating the shelf mode switch.

2. Sleep—the mode the device enters between timed wakeups. It can be awoken by either the watchdog timer or the wakeup switch.

3. Boot—the device is reading configuration settings and initializing operation. At this point, the shelf mode lockout switch is actuated, preventing the patch from returning to shelf mode without an explicit command.

4. Wake—a transient state immediately after a watchdog timer wakeup where the system decides whether to sample data, advertise for a connection or do nothing.

5. Advertising—sending advertisements and waiting for someone to connect and authenticate.

6. Acquire—In the Acquire mode, the device samples data from the ADC or I2C bus into internal buffers.

7. Transmit—in the Transmit mode, the device streams data notifications to the hub. The Transmit mode can be interrupted by the reed switch, but the device is not listening for commands.

8. Command—In the Command mode, the device listens for, or responds to commands communicated over the communication interface (e.g. Bluetooth® Low Energy (BLE) interface).

B. Flow.

The state diagram in FIG. 16B shows the flow of control between modes. Note that when the reed switch is triggered from sleep or command modes, the system is triggered to first acquire, then transmit all stored packets. This is shown here via a parameter "chain" that is set when the reed switch is triggered, and is automatically cleared upon return to command mode.

In an example implementation, each mode may operate as follows:

(1) Shelf Mode

The system is disconnected from the battery.

(2) Boot Mode

The shelf mode lockout switch is actuated, preventing the device from going back to shelf mode without an explicit command.

The processor reads a configuration settings block into a configuration data structure.

All interrupts and IO pins are initialized.

A watchdog timer is set to wake up every 1 hour, for example.

(3) Sleep Mode

The wearable patch may be put in a deep sleep mode, which refers to a function of the processor in this example, with the watchdog timer set to wake up at the next event. The wake up at the next event may be a sensor read event or an advertising wakeup, occurring after a predetermined time period, such as for example, every 1 hour.

It may be assumed that the advertising wakeup will happen more frequently than the read period, and the read period (currently, is 3 hours) will be a multiple of that time interval.

(4) Advertising

The processor turns on advertising for a selected time period, for example, 30 seconds at a selected advertising frequency, for example, 2 Hz rate. The advertising is provided for display or printout on a connectable peripheral device.

The wearable patch may be bonded to a single hub, via an LE Secure encrypted private address. Connection will automatically occur if the wearable patch is bonded. If the patch is not bonded, it will be open for pairing or commands from any hub that has the appropriate out-of-band (OOB) shared secret key.

(5) Wake

The Wake State operates as follows:

The Wake state is a transient state which evaluates the time and decides whether to acquire data or advertise in order try to make a connection to a hub. Note that data acquisition from sensors is started before an attempt is made to make a connection in order to save the power of running the PA/LNA during acquisition.

(6) Command

When a connection is made, the local hub can issue commands.

In command mode, any characteristic can be activated as described in the BLE Characteristics section below.

If a selected time period (e.g. 30 seconds) elapses after completion of the most recent command, the device automatically enters sleep mode.

(7) Acquire

Data may be captured automatically every 3 hours, or when requested via commands over the BLE interface.

To capture data, the patch may turn on power to a sensor and the onboard op amps. The patch then waits a fixed delay period, e.g. 2 seconds, for the wearable patch to stabilize. The wearable patch will then take measurements.

Data may be compressed as it arrives from the ADC or digital sensor. Data may be compressed for storage in a 251-byte buffer using a delta encoder (encoders are independent, on a per channel basis). When the buffer fills, the data may be copied to the FRAM, in time sorted order as a circular buffer-of-buffers.

(8) Transmit

Data is transmitted to the local hub at a maximum rate in 251-byte BLE 4.2 packets. Each packet may comprise its own timestamp. The system may proceed to transmit the new packets in the buffer. Once the final packet is transmitted, the wearable patch may send an END-OF-BUFFER indication.

The wearable patch may receive a command requesting transmission of all buffers. In response to receiving the command requesting transmission of all buffers, the wearable patch transmits all buffers are transmitted sequentially and marked as SENT.

FIG. 16B is a block diagram of the processor 1604 in FIG. 16A. In the example described above with reference to FIG. 3A, the processor is implemented using a Cypress PSOC BLE module, which is based on a Cortex M3 ARM core, contains 256 MB FLASH, 32 KB RAM and supports BLE 4.2.

Figure 17A:
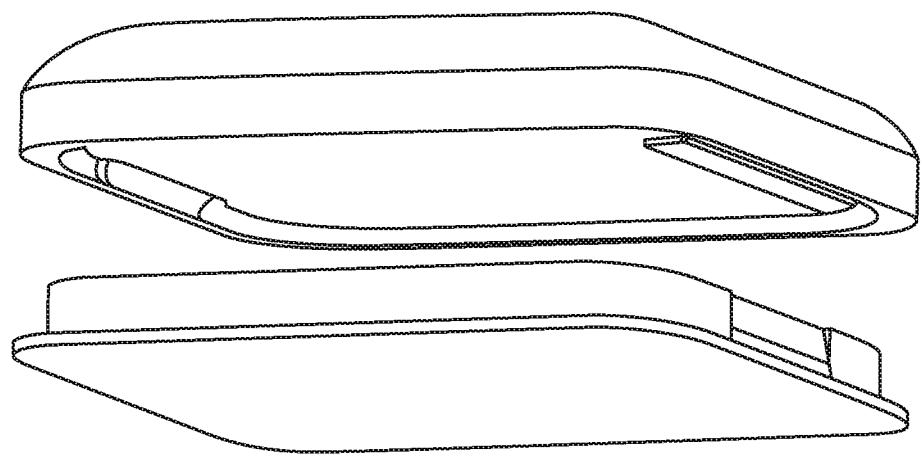
FIG. 17A is a perspective bottom view of an example of a wearable patch.
Figure 17B:
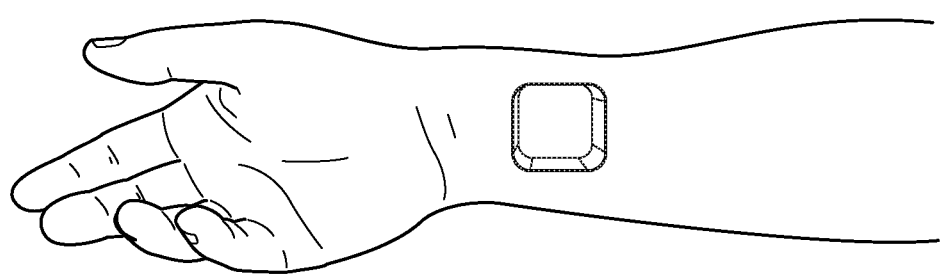
FIG. 17B is a top view of an example of a wearable patch.

FIG. 17A is a perspective bottom view of an example of a wearable patch. FIG. 17B is a top view of an example of a wearable patch attached to a patient's arm. The wearable patch is intended to be worn over a fistula and configured to communicate to a nearby sensor data processing system, which may comprise a local hub for forwarding data to a backend, or remote sensor data processor.

The wearable patch may be formed with 1 or 2 parts. FIG. 17A depicts an example wearable patch formed in 2 parts. If the wearable patch is in 1 part, then the adhesive may be a replaceable component (3-7x/week) and the device may be configured to house electronics components, while still enabling adequate coupling of the sensor to the skin for conformal attachment. If the wearable patch is formed in 2 parts, the part connected to the skin could be a flexible adhesive layer with the sensor assembly and the second part would comprise the encapsulated electronics. The mechanical features on both parts that connect the two parts would also comprise electrical connectors that would enable communication between the sensor assembly and the electronics (processor, communications interface, etc.). The mechanical features in particular on the sensor/adhesive part would be flexible to enable conformal attachment of the sensor assembly and adhesive to the skin, while still allowing for secure mating with the rigid, encapsulated electronics. The overall size of the wearable patch, including the height, may be an important factor that affects comfort. The wearable patch may be powered by a battery, which would likely be the largest component.

7. Power Consumption.

The expected power consumption of the wearable patch may help determine the size of the battery required to operate between recharges. The power may be dominated by the standby current since the duty cycle is low (3 hours off, 5 seconds on).

8. Method for Monitoring a Patient.

Determining either a thrombosis alert or level of stenosis requires a few steps of signal processing to get data from the sensor, digitized, and analyzed. The above description with reference to FIG. 16A of the example implementation of a wearable sensor comprises a detailed description of how data may be extracted from the sensors shown in FIG. 16A using the components in FIG. 16A. In general, the data extraction process involves the steps of:

1. sensing a plurality of sensory modalities using a sensor assembly comprising a plurality of sensors mounted on a wearable patch, where the sensory modalities are received as one or a plurality of electrical signals representing the sensory modalities;
2. converting the one or a plurality of electrical signals to a plurality of corresponding one or a plurality of sensor data signals; and
3. transmitting the one or a plurality of sensor data signals to a sensor data processing system.

Figure 18:
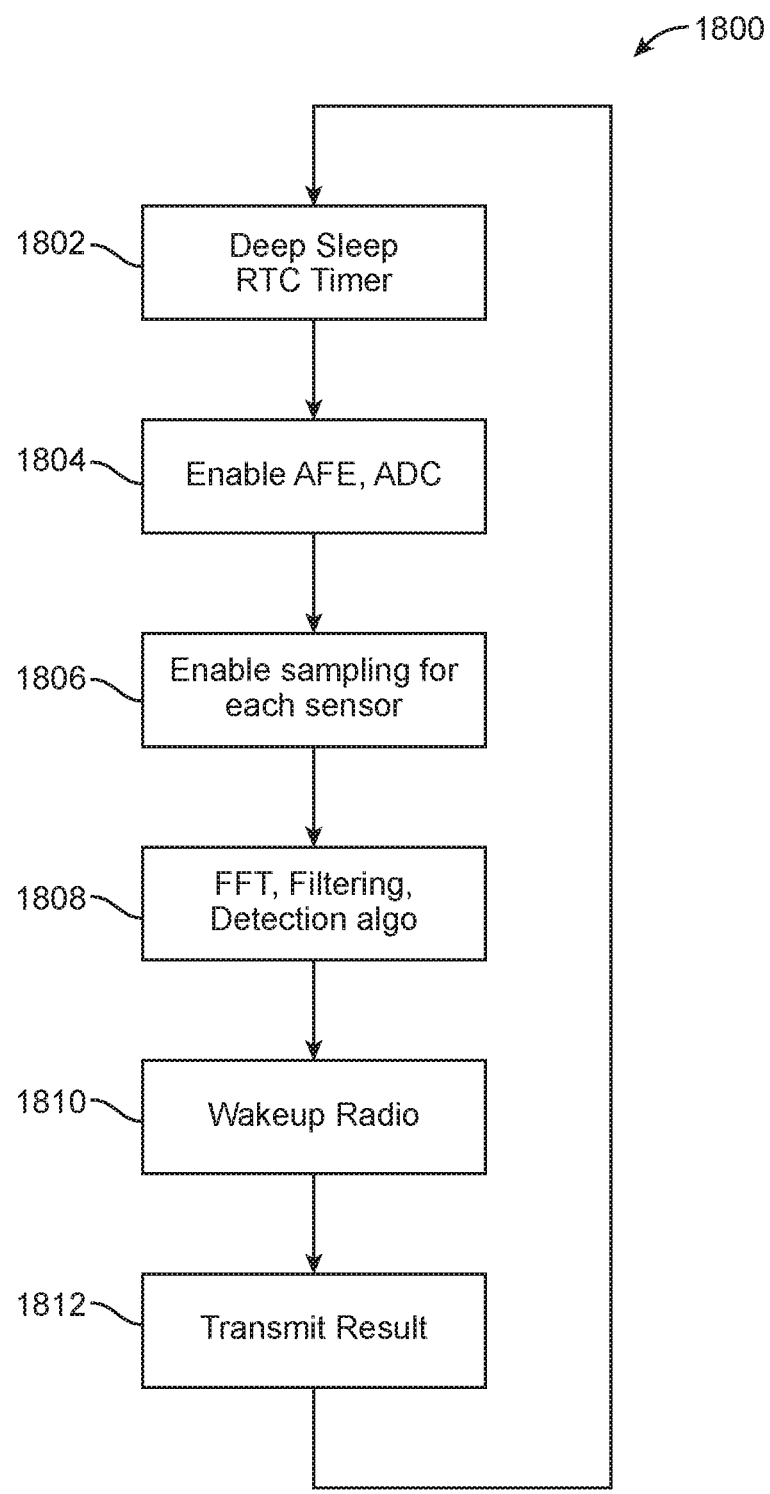
FIG. 18 is a flowchart illustrating operation of a method for monitoring subcutaneous processes in a patient wearing a wearable patch.

FIG. 18 is a flowchart illustrating operation of an example of a method for obtaining data from a sensor assembly. The method in FIG. 18 may be performed using any suitable sensor assembly connected to a signal converter, which may be implemented using a processor that uses a real time clock timer, an ADC function and signal processing capabilities including for example, Fast Fourier Transform (PFT) tools, digital filtering functions, and signal detection algorithms.

The method illustrated in FIG. 18 begins at step 1802 in which the processor is in a sleep mode, and a real-time clock (RTC) timer is set to wake the processor periodically. The processor enables the analog front end (AFE) and the ADC function at step 1804. The AFE refers to the sensor assembly, which when enabled, begins to receive sensory modalities corresponding to the sensors in the sensor assembly. The sensory modalities are converted to one or a plurality of electrical signals. Sampling may then be enabled for each sensor as indicated in step 1806. The one or a plurality of electrical signals sampled by the ADC function may be sampled at 10 k samples/sec for 2 seconds; however, the sampling rate may be adapted for each sensor modality. The digital samples representing the electrical signal from the sensors may be processed using digital signal processing functions, such as for example, the functions listed above, as deemed useful for each signal as indicated in step 1808. At step 1810, the communications interface is awakened for transmission of the sensor data. The processor generates the sensor data signal from the digital signal processing functions and formats the sensor data signal according to a suitable communication protocol. The sensor data signal is then transmitted at step 1812 via the communication interface.

The wearable patch may transmit results wirelessly after the sensing operation. In an example implementation, Bluetooth® Smart™ is a low power radio technology that may be used to communicate to a relay or local hub. The local hub transfers the results to a backend system, such as the remote sensor data processor in the network. Storage and further processing of the sensor data may be performed on the remote sensor data processor, which may be implemented on a remote server. A front-end interface may be configured to communicate alerts to a clinician.

Figure 19:
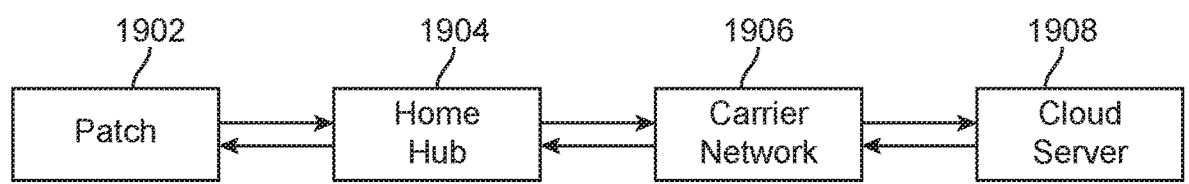
FIG. 19 is a block diagram of an example system for monitoring a patient wearing a wearable patch.

FIG. 19 is a block diagram of an example system architecture for a system for monitoring a patient wearing a wearable patch. The system in FIG. 19 comprises a patch 1902 connected to a local hub 1904 via a BLE connection. Any other suitable local communication protocol may be used as well. The local hub is connected to a carrier network 1906 using a cellular link. The carrier network is a cellular data system, but may be any other suitable network infrastructure, such as the Internet where connection to the Internet is achieved using a WiFi™ system, a hardwired Ethernet connection, or any other infrastructure that may be used for communicating remotely. In the example in FIG. 19, the carrier network connects the home hub over the Internet to an Amazon Web Service (AWS) 1908. The AWS is a cloud-based computing service. Other cloud-based services are available from Microsoft, Oracle and other, and may be used as well.

9. Determining a Level of Stenosis.

Examples of a wearable patch may be used as part of a system to monitor and alert for thrombosis development or clinically actionable levels of stenosis in a vessel such as an AV fistula or graft. Alerts may be triggered by the system and lead to a clinical pathway whereby the patient is examined by a care provider and put through a diagnostic pathway including but not limited to duplex ultrasound, fistulogram and/or arteriograms. The results of the diagnostic studies combined with the monitoring result from the patch could lead to a corrective intervention such as a drug prescription, thrombectomy or angioplasty to clear the blocked fistula. In some cases, the diagnostic process may lead to another surgery for the patient to place a new fistula, HERO graft or central venous catheter.

The wearable patch may be worn to enable an AV fistula or Graft to reach maturation, or to help lengthen the lifetime of an AV fistula or graft. The wearable patch may be worn by the patient and communicate data and alerts multiple times in a given day. The patient may remove the electronics from the patch (if the device is constructed as a two-part patch) periodically, or replace disposable components of the patch (e.g. adhesive) depending upon the specific protocol.

During a clinician or home visit, the wearable patch may be removed and charged to replenish the battery. In the case of an AV fistula patient, the battery-charging may be performed during the dialysis session.

Standard clinical protocols typically require a check of the patency of an AV fistula or graft during a physical examination on routine visits to a clinician. The clinician can "feel the thrill" of a bruit, and also listen for the bruit using a conventional stethoscope. A change of the character of the bruit to a higher pitch can indicate the presence of stenosis or thrombosis. Various methods may be used to quantify the stenosis using the digital output of a stethoscope, or to determine if a thrombosis has formed. One example is to use a break frequency to estimate the internal diameter of the carotid artery in patients. This technique is referred to as phonoangiography. The break frequency may be determined a number of ways. A frequency power spectrum may be calculated for an acoustic sensor output and used to identify the highest frequency after which the power drops off significantly. A higher break frequency is correlated with a narrower vessel, and thus a higher level of stenosis. Break frequency values typically fall between 10 and 1000 hz., where a value closer to 1000 would indicate a significant degree of stenosis (>50%). In AV fistulas, metrics such as the break frequency may be utilized to determine either thrombosis or stenosis.

A key difference may exist for the utilization of break frequency for AV fistulas as opposed to a carotid artery. In the carotid artery, a bruit is indicative of unhealthy flow, while in the AV fistula a bruit is indicative of healthy flow. Thus, the correlation in AV fistula may be reversed from those found in the carotid artery, with a lower level of bruit (i.e. a lower break frequency) indicating a higher degree of stenosis or potentially even thrombosis. Additional analytic methods are possible for AV fistulas/grafts such as using autoregression to calculate the power spectral density. The advantage of such a method is that it may be more effective at quantifying stenosis levels at lower flow rates. A combination of different analytical methods would likely be beneficial to determine the level of stenosis or if a potential thrombosis has occurred in an AV access.

The wearable stethoscope patch would enable this analysis by detecting these signals and automatically transmitting them for analysis over the course of a patient's life and treatment.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the processor. The software memory may comprise an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which comprises, for example, one or more microprocessors, general purpose processors, combinations of processors, digital signal processors (DSPs), application specific integrated circuits (ASICs), field-programmable gate array (FPGAs), etc. Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system, direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory machine memory.

It will also be understood that the term "in signal communication" or "in electrical communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may comprise physical, electrical, magnetic, electromagnetic, electro-chemical, optical, wired, or wireless connections. The signal paths may also comprise additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining physiological properties of a patient, the method comprising:

emitting a first illumination of a volume of tissue below a skin surface of a patient from a first light source a first distance from a photodetector positioned on the skin surface, where the first light source emits the first illumination at a plurality of first output intensities, each first output intensity corresponding to a first radius of a hemispherical region of influence;

receiving a first set of electrical signals representing reflection intensities communicated from the photodetector positioned to receive light reflected below the skin surface from the first illumination;

emitting a second illumination of the volume of tissue below the skin surface from a second light source a second distance from the photodetector, where the second light source emits the second illumination at a plurality of second output intensities, each second output intensity corresponding to a second radius of a hemispherical region of influence;

receiving a second set of electrical signals representing reflection intensities communicated from the photodetector to receive light reflected below the skin surface from the second illumination; and using the first set of electrical signals and the second set of electrical signals to measure a depth of a blood vessel within the volume of tissue below the skin surface.

2. The method of claim 1 where the first light source is configured to emit light at a first wavelength and the second light source is configured to emit light at a second wavelength, where:
the step of emitting the first illumination comprises applying a plurality of optical drive signals to the first light source to generate the plurality of first of output intensities at the first wavelength;
the step of receiving the first set of electrical signals comprises detecting a plurality of reflection intensities for each of the plurality of first output intensities, converting the plurality of reflection intensities to electrical signals, converting the electrical signals to digital data values corresponding to the electrical signals, and storing the digital data values of the electrical signals as the plurality of first wavelength intensities for each of the output intensities in a memory;
the step of emitting the second illumination comprises applying the plurality of optical drive signals to the second light source to generate a second plurality of intensities at the second wavelength;
the step of receiving the second set of electrical signals comprises detecting a plurality of reflection intensities for each of the second plurality of output intensities, converting the plurality of reflection intensities to electrical signals, converting the electrical signals to digital data values corresponding to the electrical signals, and storing the digital data values of the electrical signals as the plurality of second wavelength intensities for each of the output intensities in the memory;
the step of using the sets of signals to measure the depth of the blood vessel within the volume of tissue comprises determining a plurality of radii for each of the first and second illuminations corresponding to the plurality of first wavelength reflection intensities and the plurality of second wavelength reflection intensities and using the plurality of radii at each of the first and second wavelengths to determine the depth of the blood vessel.

3. The method of claim 2, further comprising:
calculating a ratio of reflection intensities by dividing the first wavelength reflection intensity by the second reflection intensity; and
when the first wavelength corresponds to a red light and the second wavelength corresponds to an infrared light, storing the ratio of reflection intensities as corresponding to an oxygenation level of a fluid in the blood vessel.

4. The method of claim 2 further comprising:
identifying signal artifacts in each of the first wavelength reflection intensities and in each of the second wavelength reflection intensities;
analyzing at each period, the signal artifacts identified in the first wavelength reflection intensities and the second wavelength reflection intensities to determine a period of time between the signal artifacts; and
using the period of time between the signal artifacts to determine a heart rate.

5. The method of claim 2 where the first light source is configured to emit light at a first wavelength and the second light source is configured to emit light at a second wavelength different from the first wavelength.

6. The method of claim 1 where the first light source is configured to emit light at a first wavelength and the second light source is configured to emit light at a second wavelength, where:
the step of emitting the first illumination comprises applying a plurality of optical drive signals to the first light source to generate the plurality of first output intensities at the first wavelength;
the step of receiving the first set of electrical signals comprises detecting a plurality of reflection intensities for each of the plurality of first plurality output intensities, converting the plurality of reflection intensities to electrical signals, converting the electrical signals to digital data values corresponding to the electrical signals, and storing the digital data values of the electrical signals as the plurality of first wavelength intensities for each of the output intensities in a memory;
the step of emitting the second illumination comprises applying the plurality of optical drive signals to the second light source to generate the plurality of second output intensities at the second wavelength;
the step of receiving the second set of electrical signals comprises detecting a plurality of reflection intensities for each of the plurality of second output intensities, converting the plurality of reflection intensities to electrical signals, converting the electrical signals to digital data values corresponding to the electrical signals, and storing the digital data values of the electrical signals as the plurality of second wavelength intensities for each of the output intensities in the memory;
the step of using the sets of signals to measure the depth of the blood vessel within the volume of tissue comprises determining a plurality of radii for each of the first and second illuminations corresponding to the plurality of first wavelength reflection intensities and the plurality of second wavelength reflection intensities;
the step of using the sets of signals to measure the depth of the blood vessel within the volume of tissue comprises analyzing the plurality of radii for the first illumination to determine a first intersection of the first hemispherical volume of the first optical radiation pattern at each of the plurality of first output intensities and the blood vessel;
the step of using the sets of signals to measure the depth of the blood vessel within the volume of tissue comprises analyzing the plurality of radii for the second illumination to determine a second intersection of the second hemispherical volume of the second optical radiation pattern at each of the plurality of second output intensities and the blood vessel; and
the step of using the sets of signals to measure the depth of the blood vessel within the volume of tissue comprises identifying the first light source as a primary light source when the first intersection is greater than the second intersection and identifying the second light source as the primary light source when the second intersection is greater than the first intersection.

7. The method of claim 6 further comprising:
moving the first and second light sources and the photodetector to a location on the skin surface in a direction transverse to the blood vessel such that the difference between the first intersection and the second intersection is expected to be less when the steps of claim 6 are repeated after moving the first light source, the second light source, and photodetector.

8. The method of claim 1 where the first light source is configured to emit light at a first wavelength selected from the group consisting of green, yellow, red and infrared.

9. The method of claim 1, further comprising determining a diameter of the vessel based on the plurality of radii at each of the first wavelength and the second wavelength.

10. A method for determining a diameter of a patient's blood vessel, the method comprising:
   emitting a first illumination of a volume of tissue below a skin surface of a patient from a first light source a first distance from a photodetector positioned on the skin surface, where the first light source emits the first illumination at a plurality of first intensities, each first intensity corresponding to a first radius of a hemispherical region of influence;
   receiving a first set of electrical signals representing reflection intensities communicated from the photodetector positioned to receive light reflected below the skin surface from the first illumination;
   emitting a second illumination of the volume of tissue below the skin surface from a second light source a second distance from the photodetector, where the second light source emits the second illumination at a plurality of second intensities, each second intensity corresponding to a second radius of a hemispherical region of influence;
   receiving a second set of electrical signals representing reflection intensities communicated from the photodetector to receive light reflected below the skin surface from the second illumination; and
   using the first set of electrical signals and the second set of electrical signals to measure a diameter of a blood vessel within the volume of tissue below the skin surface.

11. The method of claim 10 where the first light source is configured to emit light at a first wavelength and the second light source is configured to emit light at a second wavelength, where:
   the step of emitting the first illumination comprises applying a plurality of optical drive signals to the first light source to generate a first plurality of intensities at the first wavelength;
   the step of receiving the first set of electrical signals comprises detecting a plurality of reflection intensities for each of the first plurality of intensities, converting the plurality of reflection intensities to electrical signals, converting the electrical signals to digital data values corresponding to the electrical signals, and storing the digital data values of the electrical signals as the plurality of first wavelength intensities for each of the intensities in a memory;
   the step of emitting the second illumination comprises applying the plurality of optical drive signals to the second light source to generate a second plurality of intensities at the second wavelength;
   the step of receiving the second set of electrical signals comprises detecting a plurality of reflection intensities for each of the plurality of second intensities, converting the plurality of reflection intensities to electrical signals, converting the electrical signals to digital data values corresponding to the electrical signals, and storing the digital data values of the electrical signals as the plurality of second wavelength intensities for each of the output intensities in the memory;
   the step of using the sets of signals to measure fluid properties comprises determining a plurality of radii for each of the first and second illuminations corresponding to the plurality of first wavelength reflection intensities and the plurality of second wavelength reflection intensities;
   the step of using the sets of signals to measure a diameter of a blood vessel comprises measuring a diameter of the blood vessel based on the plurality of radii at each of the first wavelength and the second wavelength.

12. A method for determining a diameter of a patient's blood vessel, the method comprising:
   emitting a first illumination of a volume of tissue below a skin surface of a patient from a first light source a first distance from a photodetector positioned on the skin surface, where the first light source emits the first illumination at a plurality of first intensities, each first intensity corresponding to a first radius of a hemispherical region of influence;
   receiving a first set of electrical signals representing reflection intensities communicated from the photodetector positioned to receive light reflected below the skin surface from the first illumination;
   emitting a second illumination of the volume of tissue below the skin surface from a second light source a second distance from the photodetector, where the second light source emits the second illumination at a plurality of second intensities, each second intensity corresponding to a second radius of a hemispherical region of influence;
   receiving a second set of electrical signals representing reflection intensities communicated from the photodetector to receive light reflected below the skin surface from the second illumination; and
   using the first set of electrical signals and the second set of electrical signals to measure a depth and a diameter of a blood vessel within the volume of tissue below the skin surface.

13. The method of claim 12 where the first light source is configured to emit light at a first wavelength and the second light source is configured to emit light at a second wavelength, where:
   the step of emitting the first illumination comprises applying a plurality of optical drive signals to the first light source to generate the plurality of first intensities at the first wavelength;
   the step of receiving the first set of electrical signals comprises detecting a plurality of reflection intensities for each of the plurality of first plurality intensities, converting the plurality of reflection intensities to electrical signals, converting the electrical signals to digital data values corresponding to the electrical signals, and storing the digital data values of the electrical signals as the plurality of first wavelength intensities for each of the output intensities in a memory;
   the step of emitting the second illumination comprises applying the plurality of optical drive signals to the second light source to generate the second plurality of intensities at the second wavelength;
   the step of receiving the second set of electrical signals comprises detecting a plurality of reflection intensities for each of the second plurality of intensities, converting the plurality of reflection intensities to electrical signals, converting the electrical signals to digital data values corresponding to the electrical signals, and storing the digital data values of the electrical signals as the plurality of second wavelength intensities for each of the intensities in the memory;
   the step of using the sets of signals to measure the depth and diameter of the blood vessel within the volume of tissue comprises determining a plurality of radii for each of the first and second illuminations corresponding to the plurality of first wavelength reflection intensities and the plurality of second wavelength reflection intensities and using the plurality of radii at each of the first and second wavelengths to determine the depth of the blood vessel.

* * * * *